US012176081B2

(12) United States Patent
Lewis et al.

(10) Patent No.: US 12,176,081 B2
(45) Date of Patent: Dec. 24, 2024

(54) CUSTOMIZED EXCEPTIONS FOR INTELLIGENT PROTOCOLING

(71) Applicant: GE Precision Healthcare LLC, Wauwatosa, WI (US)

(72) Inventors: Chelsey A Lewis, Waukesha, WI (US); Bradley J Gabrielse, Brookfield, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 326 days.

(21) Appl. No.: 17/657,044

(22) Filed: Mar. 29, 2022

(65) Prior Publication Data

US 2023/0317219 A1   Oct. 5, 2023

(51) Int. Cl.
*G16H 40/60* (2018.01)
*G16H 10/60* (2018.01)
*G16H 30/20* (2018.01)

(52) U.S. Cl.
CPC ............ *G16H 10/60* (2018.01); *G16H 30/20* (2018.01)

(58) Field of Classification Search
CPC ...................................................... G16H 40/60
See application file for complete search history.

(56) References Cited

U.S. PATENT DOCUMENTS

| | | | | |
|---|---|---|---|---|
| 2012/0190962 A1* | 7/2012 | Glaser-Seidnitzer | ...................... | A61B 6/545 600/407 |
| 2016/0220844 A1* | 8/2016 | Paysan | .................... | G16H 10/60 |
| 2019/0370958 A1* | 12/2019 | Hancu | .................... | G16H 30/40 |
| 2022/0148157 A1* | 5/2022 | Prasad | .................... | G16H 30/40 |

OTHER PUBLICATIONS

"Using Clinical Decision Support for Informed Imaging Choices"; University of Michigan Health; Retrieved from the Internet Archive, Sep. 22, 2021 (Year: 2021).*
"MRI & CT Indications Guidelines"; Optimal Imaging St, Vincent's Health Care; Mar. 4, 2020 (Year: 2020).*
Google Patents | Search Results for "Imaging Protocol Selection", https://patents.google.com/?q=imaging+protocol+selection&oq=imaging+protocol+selection, last accessed Mar. 16, 2022, 2 pages.

* cited by examiner

*Primary Examiner* — John A Pauls
(74) *Attorney, Agent, or Firm* — Amin, Turocy & Watson, LLP

(57) ABSTRACT

Systems/techniques that facilitate customized exceptions for intelligent protocoling are provided. In various embodiments, a system can access a data candidate associated with a medical patient. In various aspects, the system can execute a trained machine learning model on the data candidate, thereby identifying a first medical imaging protocol to be performed by a medical imaging scanner on the medical patient. In various instances, the system can determine whether the data candidate triggers a conditional protocol exception, wherein the conditional protocol exception identifies a second medical imaging protocol that is to be implemented when a condition is satisfied by the data candidate. In various cases, the system can, in response to determining that the data candidate satisfies the condition, select the second medical imaging protocol to be performed by the medical imaging scanner on the medical patient instead of selecting the first medical imaging protocol.

20 Claims, 13 Drawing Sheets

CUSTOMIZED EXCEPTIONS FOR INTELLIGENT PROTOCOLING

TECHNICAL FIELD

The subject disclosure relates generally to intelligent protocoling, and more specifically to customized exceptions for intelligent protocoling.

BACKGROUND

Intelligent protocoling involves leveraging artificial intelligence to identify which medical imaging protocol should be used for a given medical patient. Although intelligent protocoling has demonstrated high overall accuracy in recommending medical imaging protocols, there are still situations in which such intelligent protocoling recommends incorrect medical imaging protocols.

Systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate customized exceptions for intelligent protocoling are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component that can access a data candidate associated with a medical patient. In various aspects, the computer-executable components can further comprise a model component that can execute a trained machine learning model on the data candidate. In various instances, the trained machine learning model can receive as input the data candidate and can recommend as output a first medical imaging protocol to be performed by a medical imaging scanner on the medical patient. In various cases, the computer-executable components can further comprise an exception component that can determine whether the data candidate triggers a conditional protocol exception. In various aspects, the conditional protocol exception can identify a second medical imaging protocol that is to be implemented when a condition is satisfied by the data candidate. In various instances, the computer-executable components can further comprise an execution component that can, in response to the exception component determining that the data candidate satisfies the condition, select the second medical imaging protocol to be performed by the medical imaging scanner on the medical patient and can refrain from selecting the first medical imaging protocol to be performed by the medical imaging scanner on the medical patient.

According to one or more embodiments, the above-described system can be implemented as a computer-implemented method and/or a computer program product.

DETAILED DESCRIPTION

Figure 1:
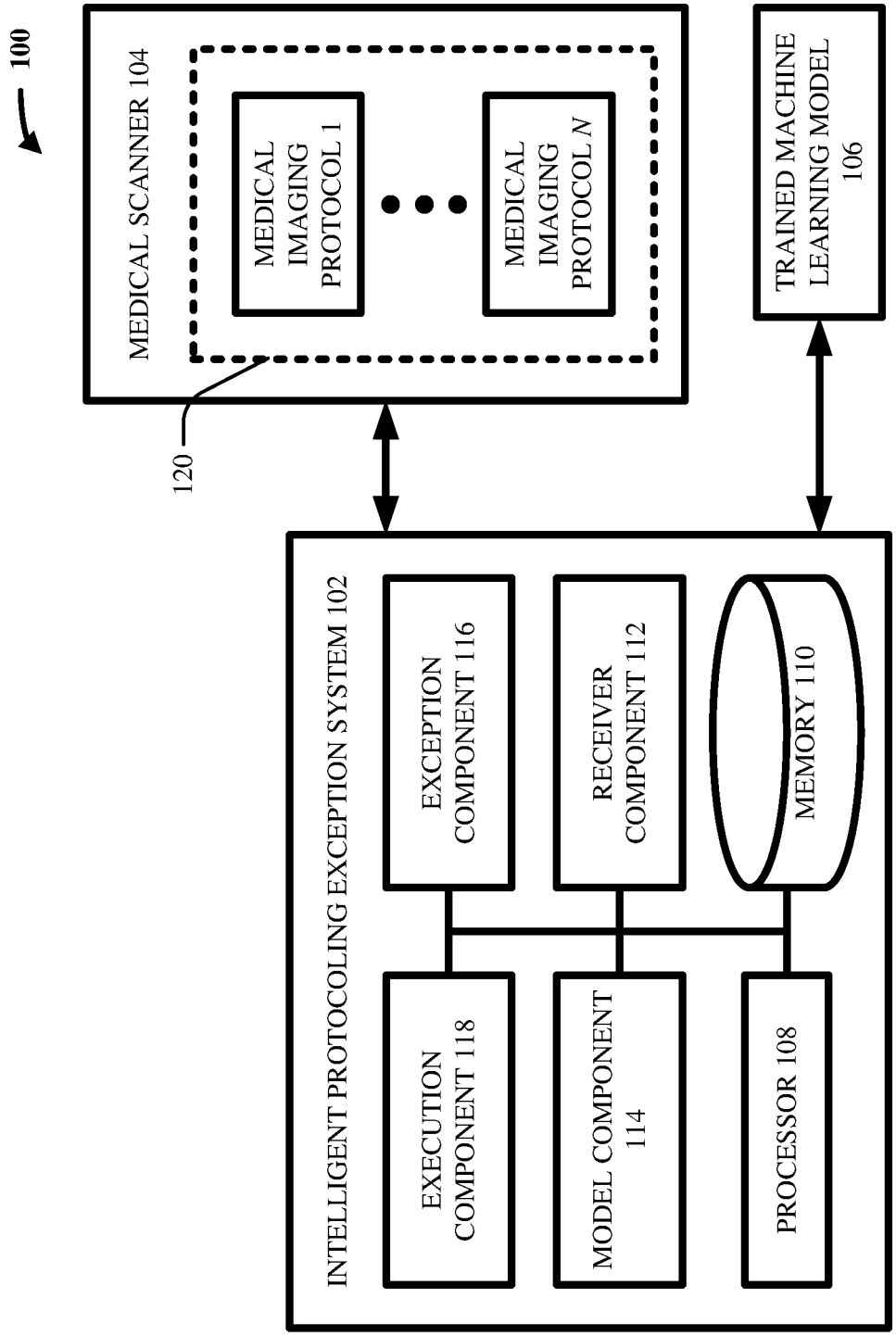
FIG. 1 illustrates a block diagram of an example, non-limiting system that facilitates customized exceptions to intelligent protocoling in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Intelligent protocoling involves leveraging artificial intelligence (e.g., deep learning neural networks) to identify which medical imaging protocol (e.g., which voltage setting, which amperage setting, which scan speed setting, which reconstruction setting) of a medical imaging scanner (e.g., a computed tomography (CT) scanner, a magnetic resonance imaging (MRI) scanner, a positron emission tomography (PET) scanner, an ultrasound scanner, an X-ray scanner) should be performed on a given medical patient (e.g., human, animal, and/or otherwise). In particular, different medical imaging protocols can be appropriate for viewing different types of biological tissues (e.g., bone tissue, brain tissue, lung tissue, muscle tissue, blood vessel tissue, cartilage tissue, calcifications). In various cases, the types of biological tissues that are desired to be viewed can depend upon a pathology and/or malady afflicting the medical patient (e.g., different tissues can be desired to be viewed when the patient is being treated for gout versus when the patient is being treated for pneumonia or when the patient is instead being treated for a broken bone). Moreover, the types of biological tissues that are desired to be viewed can also depend upon various other characteristics and/or demographics of the medical patient (e.g., patient age, patient sex, patient height, patient weight, patient body composition, patient body mass index, patient body position/orientation, patient heartrate, patient breathing rate, patient body temperature, patient implants, patient prostheses, patient surgical history, patient disease history, patient medication history, patient diet). Accordingly, electronic data that indicates a pathology/malady of a certain medical patient and/or that indicates such various other characteristics/demographics of the certain medical patient can be fed as input to an intelligent protocoling model, and the intelligent protocoling model can identify as output which medical imaging protocol should be used for the certain medical patient. The identified medical imaging protocol can be considered as a medical imaging protocol that is recommended for the certain medical patient by the intelligent protocoling model.

Although intelligent protocoling has demonstrated high overall accuracy in recommending medical imaging protocols, there still remain situations in which such intelligent protocoling recommends incorrect medical imaging protocols. In other words, despite undergoing training, intelligent protocoling nevertheless sometimes produces incorrect and/or inaccurate recommendations.

Accordingly, systems and/or techniques that can address one or more of these technical problems can be desirable.

Various embodiments described herein can address one or more of these technical problems. One or more embodiments described herein can include systems, computer-implemented methods, apparatus, and/or computer program products that can facilitate customized exceptions to intelligent protocoling. More specifically, the inventors of various embodiments described herein recognized why intelligent protocoling, notwithstanding being trained, can still yield some incorrect/inaccurate recommendations.

First, the present inventors realized that there can be certain situations that are not captured and/or represented at all in the data on which an intelligent protocoling model is trained. For example, the intelligent protocoling model cannot be expected to accurately reflect new/recent changes to medical practice that occur after the intelligent protocoling model has been trained (e.g., at the time of training, the medical community can conclude that a particular medical imaging protocol is best when given a particular patient scenario, and the intelligent protocoling model can be trained accordingly; after the time of training, the medical community can change course and instead decide that a different medical imaging protocol is actually best when given that same particular patient scenario; unfortunately, the intelligent protocoling model cannot reflect this change).

Second, the present inventors realized that there can be situations that, although captured/represented by the data on which the intelligent protocoling model is trained, are so rare and/or idiosyncratic such that the intelligent protocoling model cannot confidently learn them. For example, suppose that the data on which the intelligent protocoling model is trained indicates that a first medical imaging protocol is recommended 95% of the time when given a certain patient scenario and that a second medical imaging protocol is recommended the remaining 5% of the time when given that same certain patient scenario. Accordingly, once trained on such data, the intelligent protocoling model will always recommend (e.g., with 95% confidence) the first medical imaging protocol for that certain patient scenario and will never recommend the second medical imaging protocol for that certain patient scenario. The present inventors realized that such rare and/or idiosyncratic situations can be due to one or more hidden variables that are unknown to the intelligent protocoling model. Non-limiting examples of such hidden variables can be identity of attending physician (e.g., different physicians might prefer different medical imaging protocols for a same patient scenario), time of day (e.g., different times of day can be associated with different costs and/or availabilities of electricity; since different medical imaging protocols can use different amounts of electricity, different times of day can require different imaging protocols for a same patient scenario), and/or medical scanner version (e.g., different hardware/software versions and/or model years of medical scanners can have different available medical imaging settings, depending upon how updated and/or how outdated such medical scanners are; thus, different medical scanner versions and/or model years can require different medical imaging protocols for a same patient scenario).

In any case, the present inventors realized that certain situations that are either not captured/represented in the training data of an intelligent protocoling model, or that are so rare/idiosyncratic as to be unable to be confidently learned by the intelligent protocoling model, can cause the intelligent protocoling model to generate inaccurate recommendations. Accordingly, the present inventors devised various embodiments described herein to deal with such situations.

In various aspects, various embodiments described herein can be considered as a computerized tool (e.g., any suitable combination of computer-executable hardware and/or computer-executable software) that can facilitate customized exceptions to intelligent protocoling. In various instances, when given electronic data describing a medical patient scenario, such computerized tool can execute a trained intelligent protocoling model on such electronic data, thereby identifying which medical imaging protocol is recommended by the intelligent protocoling model. Moreover, such computerized tool can also determine whether or not such electronic data triggers any of one or more conditional exceptions that are applicable to the intelligent protocoling model, where each conditional exception identifies a respectively corresponding alternative medical imaging protocol that is to be implemented when a respectively corresponding condition is satisfied. In various cases, the one or more conditional exceptions can cover and/or apply to situations that are either not captured/represented in the training data of the intelligent protocoling model or that are so rare/idiosyncratic as to be unable to be confidently learned by the intelligent protocoling model. Accordingly, if the electronic data does not trigger any of the one or more conditional exceptions, the computerized tool can schedule, implement, and/or otherwise auto-select the medical imaging protocol recommended by the intelligent protocoling model. On the other hand, if the electronic data triggers any of the one or more conditional exceptions, the computerized tool can schedule, implement, and/or auto-select a different medical imaging protocol than that recommended by the intelligent protocoling model. Therefore, in various cases, the computerized tool can be considered as a safety net and/or backstop that can catch and/or otherwise deal with situations in which the intelligent protocoling model is likely to make an inaccurate recommendation (e.g., situations that are not captured/represented in the training data at all, and/or situations that are captured/represented in the training data but that are so rare/idiosyncratic as to be unable to be confidently learned).

In various embodiments, the computerized tool described herein can comprise a receiver component, a model component, an exception component, and/or an execution component.

In various embodiments, there can be a medical scanner and/or a trained intelligent protocoling model. In various aspects, the medical scanner can be any suitable medical imaging device (e.g., CT scanner, MRI scanner, PET scanner, ultrasound scanner, X-ray scanner). In various instances, the medical scanner can perform any of a plurality of medical imaging protocols. In other words, the medical scanner can be configured to capture medical images (e.g., CT images, MRI images, PET images, ultrasound images, X-ray images) of a medical patient (and/or of an anatomical structure of a medical patient) according to different voltage settings, different amperage settings, different scan speed settings, and/or different reconstruction settings.

In various aspects, the trained intelligent protocoling model can exhibit any suitable machine learning architecture. For example, the trained intelligent protocoling model can exhibit a neural network architecture. In such case, the trained intelligent protocoling model can include any suitable number of layers (e.g., input layer, one or more hidden layers, output layer), any suitable numbers of neurons in various layers (e.g., different layers can have the same and/or different numbers of neurons as each other), any suitable activation functions (e.g., softmax, sigmoid, hyperbolic tangent, rectified linear unit) in various neurons (e.g., different neurons can have the same and/or different activation functions as each other), and/or any suitable inter-neuron connections (e.g., forward connections, skip connections, recurrent connections). In other instances, the trained intelligent protocoling model can exhibit any other suitable machine learning architecture (e.g., support vector machine, naïve Bayes, linear regression, logistic regression, decision tree, random forest). In any case, the trained intelligent protocoling model can be configured to receive as input electronic data pertaining to a medical patient, and to generate as output a recommendation that indicates/identifies which particular medical imaging protocol of the medical scanner should be used for and/or applied to that medical patient.

In various aspects, as mentioned above, there can be certain situations in which the trained intelligent protocoling model can incorrectly/inaccurately recommend medical imaging protocols of the medical scanner. Despite such situations, it can be desirable for an accurate/correct medical imaging protocol to be implemented by the medical scanner. As described herein, the computerized tool can help to ensure that accurate/correct medical imaging protocols are implemented by the medical scanner, notwithstanding inaccurate/incorrect recommendations provided by the trained intelligent protocoling model.

In various embodiments, the receiver component of the computerized tool can electronically receive and/or otherwise electronically access a data candidate. In some instances, the receiver component can electronically retrieve the data candidate from any suitable centralized and/or decentralized data structure (e.g., graph data structure, relational data structure, hybrid data structure), whether remote from and/or local to the receiver component. In any case, the receiver component can electronically obtain and/or access the data candidate, such that other components of the computerized tool can electronically interact with (e.g., read, write, edit, manipulate) the data candidate.

In various aspects, the data candidate can be any suitable electronic data that identifies, indicates, conveys, and/or otherwise represents information pertaining to a medical patient. In various instances, the data candidate can exhibit any suitable format and/or dimensionality. For example, the data candidate can include one or more scalars, one or more vectors, one or more matrices, one or more tensors, one or more character strings, and/or any suitable combination thereof. In various cases, the data candidate can convey any suitable type of information regarding the medical patient. For example, in some cases, the data candidate can indicate, represent, and/or convey a pathology and/or malady afflicting the medical patient, symptoms of the medical patient, an age of the medical patient, a height of the medical patient, a weight of the medical patient, a body composition of the medical patient, a blood type of the medical patient, a heartrate of the medical patient, a breathing rate of the medical patient, a temperature of the medical patient, a surgical history of the medical patient, a disease history of the medical patient, a medication history of the medical patient, a diet of the medical patient, and/or an implant of the medical patient. In various aspects, the data candidate can convey any other suitable type of information as desired. For example, the data candidate can indicate, represent, and/or convey an identity of a medical professional that is overseeing/treating the medical patient, a location/address of a healthcare facility that is treating the medical patient, a time of day for which a medical imaging scan is desired/planned for the medical patient, and/or a hardware version and/or software version of the medical scanner. In various instances, the data candidate can be generated in any suitable fashion and/or conglomerated from any suitable sources as desired (e.g., from one or more medical databases, from one or more biometric sensors that are monitoring the medical patient in real-time, from one or more cameras that are viewing the medical patient in real-time, and/or from one or more user-interfaces and/or input devices).

In various embodiments, the model component of the computerized tool can electronically identify a recommended medical imaging protocol (e.g., one of the plurality of medical imaging protocols implementable by the medical scanner) for the medical patient, by electronically executing the trained intelligent protocoling model on the data candidate (and/or on any suitable subset of the data candidate). For instance, if the trained intelligent protocoling model exhibits a neural network architecture, then the model component can feed the data candidate (and/or any suitable subset/portion thereof) to an input layer of the trained intelligent protocoling model, the data candidate (and/or any suitable subset/portion thereof) can complete a forward pass through one or more hidden layers of the trained intelligent protocoling model, and/or an output layer of the trained intelligent protocoling model can compute a categorical classification and/or label based on activations provided by the one or more hidden layers. In various cases, the categorical classification/label can indicate, identify, and/or otherwise convey the recommended medical imaging protocol (e.g., can indicate, identify, and/or otherwise convey which of the plurality of medical imaging protocols is recommended for the medical patient).

In various embodiments, the exception component of the computerized tool can electronically store, electronically maintain, and/or otherwise electronically access a conditional protocol exception. In various aspects, the conditional protocol exception can be any suitable electronic data that includes a condition and an indication of an alternative medical imaging protocol. In various instances, the alternative medical imaging protocol can be one of the plurality of medical imaging protocols that is different from the recommended medical imaging protocol (e.g., that is different from the protocol identified/recommended by the trained intelligent protocoling model). In various cases, the conditional protocol exception can be considered as an electronic instruction and/or command to use/implement the alternative medical imaging protocol (as opposed to the recommended medical imaging protocol) when the condition is satisfied by the data candidate. In various aspects, the condition, which can be referred to as a logical condition and/or as a condition precedent, can be considered as one or more expressions composed of Boolean operators and/or logical operators that are applicable to the data candidate (and/or to any suitable subset/portion thereof) so as to yield a truth value. In other words, the condition can relate to the data candidate, and the condition can either be true or false. As a non-limiting example, the condition can state that a first element of the data candidate is greater than or equal to a first threshold value and can also state that a second element of the data candidate is less than a second threshold value. If the first element of the data candidate is indeed greater than or equal to the first threshold value, and if the second element of the data candidate is indeed less than the second threshold value, then the condition can have a true truth value; that is, the data candidate can be considered as satisfying the condition. On the other hand, if the first element of the data candidate is not actually greater than or equal to the first threshold value, or if the second element of the data candidate is not actually less than the second threshold value, then the condition can have a false truth value; that is, the data candidate can be considered as failing to satisfy the condition.

In some aspects, as mentioned above, the trained intelligent protocoling model can be configured to receive as input some portion of the data candidate, rather than the full/entire data candidate. In such case, the condition can, in various instances, pertain and/or apply to a remainder of the data candidate (e.g., to a different portion of the data candidate which the trained intelligent protocoling model is not configured to receive as input). Accordingly, in such case, the condition can be considered as applying to information that is unknown and/or unknowable to the trained intelligent protocoling model (e.g., the condition can be considered as applying to hidden variables that are not seen by the trained intelligent protocoling model). For example, the data candidate can include a medical history of the medical patient, a pathology of the medical patient, an identity of a physician attending to the medical patient, and/or a hardware software version identifier of the medical scanner. In such case, the trained intelligent protocoling model can be configured to receive as input a portion of the data candidate that indicates the medical history and the pathology, but can be configured to not receive as input a remainder of the data candidate that indicates the physician identifier and the hardware/software version identifier. Accordingly, in various aspects, the condition can pertain to the physician identifier and/or to the hardware/software version identifier, which can be considered as variables that are hidden from the trained intelligent protocoling model.

In any case, the exception component can electronically determine whether or not the data candidate triggers the conditional protocol exception. That is, the exception component can apply the condition to the data candidate, so as to determine whether or not the data candidate satisfies the condition (e.g., so as resolve the truth value of the condition with respect to the data candidate).

In various embodiments, the execution component of the computerized tool can take any suitable electronic action based on the determination made by the exception component. For example, in response to the exception component determining that the data candidate does not trigger the conditional protocol exception (e.g., in response to the exception component determining that the data candidate does not satisfy the condition), the execution component can electronically select and/or implement the recommended medical imaging protocol instead of the alternative medical imaging protocol. That is, the execution component can electronically cause, instruct, and/or schedule the medical scanner to perform the recommended medical imaging protocol and not the alternative medical imaging protocol. In cases where manual selection by a technologist is utilized, the execution component can render, on any suitable computer display/monitor/screen, the plurality of medical imaging protocols in a list that is viewable to the technologist, and the execution component can highlight the recommended medical imaging protocol in such list and/or can gray-out and/or hide all other medical imaging protocols in such list, thereby visually conveying to the technologist that the recommended medical imaging protocol should be selected for the medical patient.

On the other hand, in response to the exception component determining that the data candidate does trigger the conditional protocol exception (e.g., in response to the exception component determining that the data candidate does satisfy the condition), the execution component can electronically select and/or implement the alternative medical imaging protocol instead of the recommended medical imaging protocol. That is, the execution component can electronically cause, instruct, and/or schedule the medical scanner to perform the alternative medical imaging protocol and not the recommended medical imaging protocol. In cases where manual selection by a technologist is utilized, the execution component can render, on any suitable computer display/monitor/screen, the plurality of medical imaging protocols in a list that is viewable to the technologist, and the execution component can highlight the alternative medical imaging protocol in such list and/or can gray-out and/or hide all other medical imaging protocols in such list, thereby conveying to the technologist that the alternative medical imaging protocol should be selected for the medical patient.

In some embodiments, the computerized tool can further comprise a training component. In various aspects, the training component can electronically train, in supervised fashion, the trained intelligent protocoling model based on the alternative medical imaging protocol. For example, suppose that the exception component determines that the data candidate triggers the conditional protocol exception. In such case, the recommended medical imaging protocol can be considered as being inaccurate/incorrect with respect to the data candidate, and the alternative medical imaging protocol can be considered as being correct/accurate with respect to the data candidate. Accordingly, the alternative medical imaging protocol can, in some instances, be considered as a ground-truth label/annotation that is known and/or deemed to correspond to the data candidate, and the recommended medical imaging protocol can be considered as an incorrect output generated by the trained intelligent protocoling model based on the data candidate. Therefore, in various aspects, the training component can compute a difference, error, and/or loss between the recommended medical imaging protocol and the alternative medical imaging protocol, and the training component can electronically update (e.g., via backpropagation) internal parameters (e.g., weights, biases) of the trained intelligent protocoling model based on such error/loss. In other words, the training component can update and/or overwrite the learning of the trained intelligent protocoling model, so as to help improve the accuracy of the trained intelligent protocoling model.

In various aspects, the conditional protocol exception can be user-defined. For example, the conditional protocol exception can be manually coded and/or otherwise inputted into and/or via any suitable user-interface device (e.g., keyboard, touchscreen, voice command, keypad, joystick). Thus, users and/or operators of the computerized tool can manually create customized conditional protocol exceptions as desired.

In various other aspects, the exception component can automatically generate the conditional protocol exception based on a statistical analysis of past and/or prior manual overrides associated with the trained intelligent protocoling model. For example, as mentioned above, the trained intelligent protocoling model can be considered as recommending which of the plurality of medical imaging protocols it believes should be applied to individual medical patients. In some cases, a medical professional and/or technologist that is overseeing the medical patient and/or that is operating the medical scanner can choose to follow the recommendations of the trained intelligent protocoling model. In other cases, the medical professional and/or technologist can instead choose protocols other than those recommended by the trained intelligent protocoling model. In some instances, the computerized tool can comprise an insight component which can electronically record, log, and/or otherwise track whether the medical professional/technologist chooses to follow the recommendations of the trained intelligent protocoling model. Such recording, logging, and/or tracking can result in a rich set of data, which can be referred to as an insight dataset, that can be mined and/or analyzed for insights regarding when the medical professional/technologist chooses to follow, or chooses to ignore, the recommendation of the trained intelligent protocoling model.

More specifically, the insight dataset can include a set of prior data candidates received by the receiver component and/or a set of manual override indicators that respectively correspond to the set of prior data candidates. In various aspects, each manual override indicator can convey whether or not a recommendation of the trained intelligent protocoling model for a respectively corresponding prior data candidate was manually overridden. In other words, each manual override indicator can be any suitable electronic data that conveys whether a medical professional/technologist followed or ignored the trained intelligent protocoling model's recommendation for a respective prior data candidate (e.g., each manual override indicator can convey both the recommended protocol and the manually selected protocol for a respective prior data candidate).

In various instances, the exception component can generate the conditional protocol exception by analyzing the insight dataset via any suitable statistical techniques as desired (e.g., computation of means, medians, modes, and/or proportions; application of iterative clustering and/or grouping techniques). For instance, in some cases, the exception component can generate a conditional protocol exception (or can suggest that a conditional protocol exception be generated) when a computed percentage/proportion of the insight dataset is above any suitable threshold level. As a non-limiting example, consider a threshold proportion level of 60%, and suppose that the insight dataset indicates that a medical imaging protocol A was manually selected 86% of the time when prior medical patients were being treated for pneumonia by Dr. John Doe, regardless of the recommendation of the trained intelligent protocoling model. Because 86% is greater than the threshold proportion level of 60%, the exception component can electronically generate (and/or can electronically suggest the generation of) a conditional protocol exception which calls for the medical imaging protocol A when a medical patient is being treated for pneumonia by Dr. John Doe.

Accordingly, various embodiments described herein can be considered as a computerized tool that can electronically implement conditional protocol exceptions so as to handle situations in which a trained intelligent protocoling model might inaccurately/incorrectly recommend medical imaging protocols.

Various embodiments described herein can be employed to use hardware and/or software to solve problems that are highly technical in nature (e.g., to facilitate customized exceptions for intelligent protocoling), that are not abstract and that cannot be performed as a set of mental acts by a human. Further, some of the processes performed can be performed by a specialized computer (e.g., medical imaging scanner, neural network) for carrying out defined tasks related to customized exceptions for intelligent protocoling. For example, such defined tasks can include: accessing, by a device operatively coupled to a processor, a data candidate associated with a medical patient; executing, by the device, a trained machine learning model on the data candidate, wherein the trained machine learning model receives as input the data candidate, and wherein the trained machine learning model recommends as output a first medical imaging protocol to be performed by a medical imaging scanner on the medical patient; determining, by the device, whether the data candidate triggers a conditional protocol exception, wherein the conditional protocol exception identifies a second medical imaging protocol that is to be implemented when a condition is satisfied by the data candidate; and/or in response to a determination that the data candidate satisfies the condition, selecting, by the device, the second medical imaging protocol to be performed by the medical imaging scanner on the medical patient and refraining, by the device, from selecting the first medical imaging protocol to be performed by the medical imaging scanner on the medical patient.

Such defined tasks are not performed manually by humans. Indeed, neither the human mind nor a human with pen and paper can electronically execute a neural network on medical data to yield a recommended medical imaging protocol, can electronically determine whether the medical data triggers a conditional protocol exception that identifies an alternative medical imaging protocol, and/or electronically select/execute the alternative medical imaging protocol instead of the recommended medical imaging protocol when the conditional protocol exception is triggered. Instead, various embodiments described herein are inherently and inextricably tied to computer technology and cannot be implemented outside of a computing environment (e.g., a medical imaging scanner is an inherently-computerized device that can generate medical images by passing radiation through an object of interest, such as an anatomical structure of a patient; a neural network is also an inherently computerized device that can be trained to identify which protocols of the medical imaging scanner to implement for specific patients; a computerized tool that can leverage conditional exceptions so as to handle incorrect/inaccurate recommendations produced by the neural network is likewise inherently-computerized and cannot be implemented in any sensible, practical, or reasonable way without computers).

Moreover, various embodiments can integrate into a practical application various teachings described herein relating to customized exceptions for intelligent protocoling. As explained above, an intelligent protocoling model can, notwithstanding having undergone training, generate inaccurate/incorrect recommendations. As the present inventors recognized, such inaccurate/incorrect recommendations can arise in situations that are not captured/represented in the data that was used to train the intelligent protocoling model, and/or can arise in situations that are captured/represented in such training data but that are so rare/idiosyncratic as to be unable to be confidently learned by the intelligent protocoling model. The present inventors devised various embodiments described herein, which can act as a safety net and/or a backstop that catches and/or handles such situations in which the intelligent protocoling model is likely to make inaccurate/incorrect recommendations. More specifically, the computerized tool described herein can receive data pertaining to a medical patient and can execute the intelligent protocoling model on such data, thereby yielding a recommended medical imaging protocol. Moreover, the computerized tool can store, maintain, and/or access a conditional protocol exception that identifies an alternative medical imaging protocol to be implemented when a condition is satisfied. In various cases, the condition can pertain to and/or describe a situation that is not covered by the data on which the intelligent protocoling model was trained, and/or can pertain to and/or describe a situation that is covered by the data on which the intelligent protocoling model was trained but that was too rare and/or idiosyncratic to be confidently learned by the intelligent protocoling model. Specifically, in some cases, the condition can pertain to variables and/or information that are hidden from and/or unknowable to the intelligent protocoling model. In any case, the computerized tool can electronically determine whether the data pertaining to the medical patient satisfies the condition. If so, the computerized tool can execute and/or auto-select the alternative medical imaging protocol rather than the recommended medical imaging protocol. If not, the computerized tool can execute and/or auto-select the recommended medical imaging protocol rather than the alternative medical imaging protocol. Such a computerized tool can serve as a safety net and/or redundant backstop that helps to protect against inaccurate/incorrect recommendations provided by the intelligent protocoling model. Thus, such a computerized tool certainly constitutes a concrete and tangible technical improvement in the field of intelligent protocoling, and thus surely qualifies as a useful and practical application of computers.

Furthermore, various embodiments described herein can control real-world tangible devices based on the disclosed teachings. For example, various embodiments described herein can electronically control (e.g., power up, power down, calibrate, engage, disengage) real-world medical imaging scanners (e.g., CT scanners, MRI scanners, PET scanners, ultrasound scanners, X-ray scanners) based on results provided by real-world neural networks and/or based on truth values of real-world Boolean expressions.

It should be appreciated that the herein figures and description provide non-limiting examples and are not necessarily drawn to scale.

FIG. 1 illustrates a block diagram of an example, non-limiting system 100 that can facilitate customized exceptions to intelligent protocoling in accordance with one or more embodiments described herein. As shown, an intelligent protocoling exception system 102 can be electronically integrated, via any suitable wired and/or wireless electronic connections, with a medical scanner 104 and/or with a trained machine learning model 106.

In various embodiments, the medical scanner 104 can be any suitable medical imaging device as desired. For example, the medical scanner 104 can be a CT scanner. As another example, the medical scanner 104 can be an MRI scanner. As still another example, the medical scanner 104 can be a PET scanner. As yet another example, the medical scanner 104 can be an ultrasound scanner. As even another example, the medical scanner 104 can be an X-ray scanner. In any case, the medical scanner 104 can implement any of a set of medical imaging protocols 120. In various instances, as shown, the set of medical imaging protocols 120 can include n protocols for any suitable positive integer n: a medical imaging protocol 1 to a medical imaging protocol n. In various aspects, each of the set of medical imaging protocols 120 can be considered as being, pertaining to, and/or describing different configurable/controllable settings/parameters of the medical scanner 104. As some non-limiting examples, such configurable/controllable settings/parameters can include a voltage setting/parameter of the medical scanner 104, an amperage setting/parameter of the medical scanner 104, a scan speed setting/parameter of the medical scanner 104, and/or a reconstruction setting/parameter of the medical scanner 104. So, in various cases, the medical imaging protocol 1 can be considered as representing an operation (e.g., a scan) that is performable by the medical scanner 104 when the medical scanner 104 is configured with a first voltage setting, a first amperage setting, a first scan speed setting, and/or a first reconstruction setting. Likewise, in various instances, the medical imaging protocol n can be considered as representing an operation (e.g., a scan) that is performable by the medical scanner 104 when the medical scanner 104 is configured with an n-th voltage setting, an n-th amperage setting, an n-th scan speed setting, and/or an n-th reconstruction setting. In some cases, the set of medical imaging protocols 120 can be considered as a set of protocols that are available to be performed/executed by the medical scanner 104.

In various aspects, the trained machine learning model 106 can exhibit any suitable artificial intelligent architecture as desired. As a non-limiting example, the trained machine learning model 106 can exhibit a deep learning neural network architecture. That is, the trained machine learning model 106 can have any suitable number of layers, any suitable numbers of neurons in various layers, any suitable activation functions in various neurons, and/or any suitable inter-neuron connection patterns. Various other non-limiting examples of the architecture of the trained machine learning model 106 can include a support vector machine architecture, a naïve Bayes architecture, a linear and/or logistic regression architecture, a decision tree architecture, and/or a random forest architecture. In any case, the trained machine learning model 106 can be configured to receive as input any suitable electronic data pertaining to any given medical patient and to produce as output a classification/label that identifies a recommended medical imaging protocol for that given medical patient. In other words, the trained machine learning model 106 can be considered as identifying which of the set of medical imaging protocols 120 is most recommended, suggested, and/or appropriate for that given medical patient. As those having ordinary skill in the art will appreciate, the trained machine learning model 106 can have been trained in any suitable fashion as desired (e.g., in supervised fashion, in unsupervised fashion, in reinforcement learning fashion).

In various instances, although the trained machine learning model 106 can have been trained, there can still be certain situations in which the trained machine learning model 106 can inaccurately/incorrectly recommend medical imaging protocols. In various cases as described herein, the intelligent protocoling exception system 102 can handle and/or deal with such situations, so as to help ensure that correct/accurate medical imaging protocols are implemented by the medical scanner 104 notwithstanding such incorrectness/inaccuracy of the trained machine learning model 106.

In various embodiments, the intelligent protocoling exception system 102 can comprise a processor 108 (e.g., computer processing unit, microprocessor) and a computer-readable memory 110 that is operably and/or operatively and/or communicatively connected/coupled to the processor 108. The computer-readable memory 110 can store computer-executable instructions which, upon execution by the processor 108, can cause the processor 108 and/or other components of the intelligent protocoling exception system 102 (e.g., receiver component 112, model component 114, exception component 116, and/or execution component 118) to perform one or more acts. In various embodiments, the computer-readable memory 110 can store computer-executable components (e.g., receiver component 112, model component 114, exception component 116, and/or execution component 118), and the processor 108 can execute the computer-executable components.

In various embodiments, the intelligent protocoling exception system 102 can comprise a receiver component 112. In various aspects, as described herein, the receiver component 112 can electronically receive a data candidate associated with a medical patient.

In various embodiments, the intelligent protocoling exception system 102 can further comprise a model component 114. In various instances, as described herein, the model component 114 can electronically execute the trained machine learning model 106 on the data candidate, so as to identify a recommended medical imaging protocol from the set of medical imaging protocols 120.

In various embodiments, the intelligent protocoling exception system 102 can further comprise an exception component 116. In various cases, as described herein, the exception component 116 can electronically determine whether the data candidate triggers a conditional protocol exception.

In various embodiments, the intelligent protocoling exception system 102 can further comprise an execution component 118. In various aspects, as described herein, the execution component 118 can electronically cause the medical scanner 104 to perform an alternative medical imaging protocol identified by the conditional protocol exception, instead of the recommended medical imaging protocol, in response to the exception component 116 determining that the data candidate triggers the conditional protocol exception.

Figure 2:
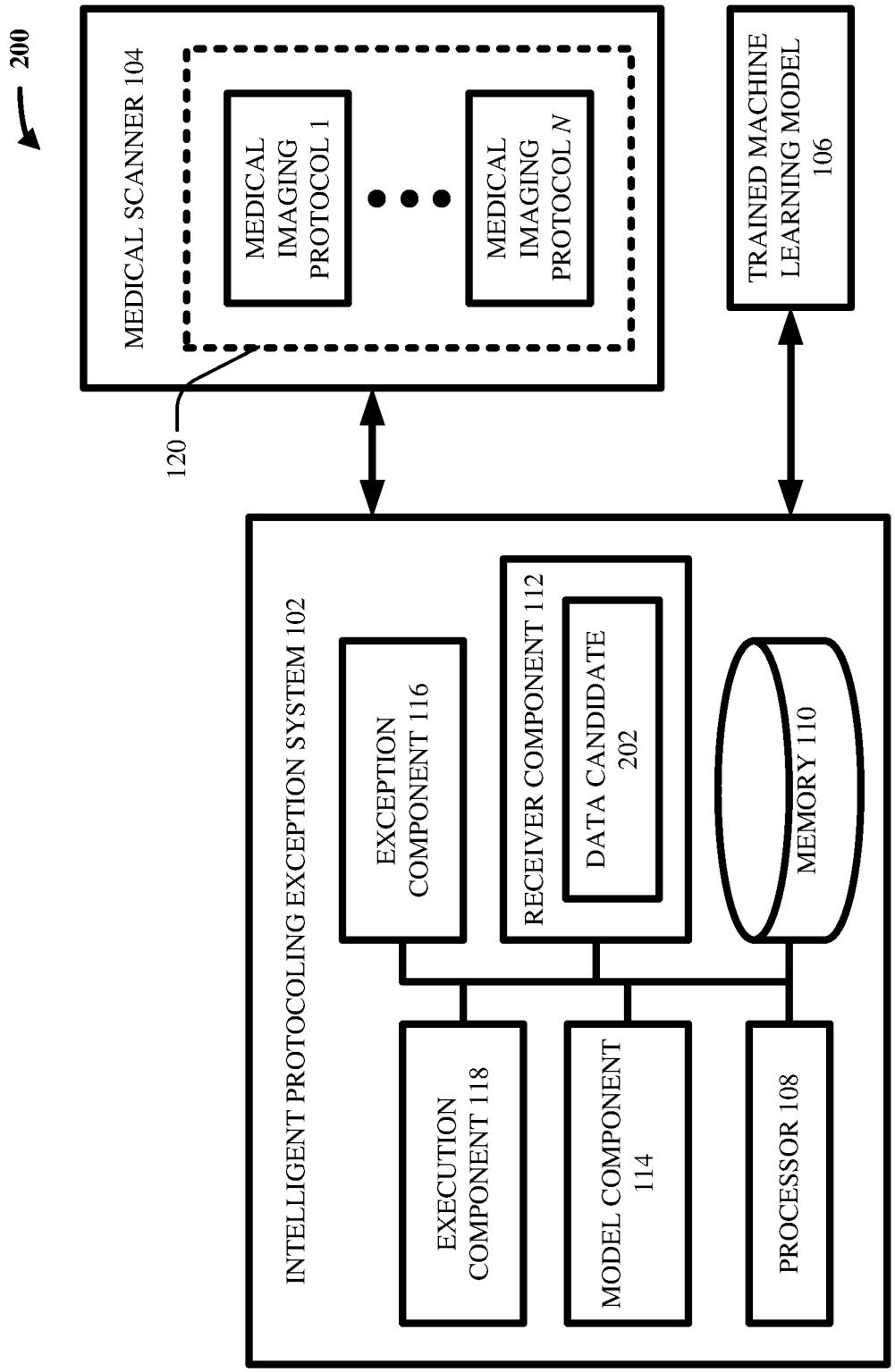
FIG. 2 illustrates a block diagram of an example, non-limiting system including a data candidate that facilitates customized exceptions to intelligent protocoling in accordance with one or more embodiments described herein.

FIG. 2 illustrates a block diagram of an example, non-limiting system 200 including a data candidate that can facilitate customized exceptions to intelligent protocoling in accordance with one or more embodiments described herein. As shown, the system 200 can, in some cases, comprise the same components as the system 100, and can further comprise a data candidate 202.

In various embodiments, the receiver component 112 can electronically receive and/or otherwise electronically access the data candidate 202. In various instances, the receiver component 112 can electronically retrieve the data candidate 202 from any suitable centralized and/or decentralized data structure (not shown), whether remote from and/or local to the receiver component 112. In various other instances, the receiver component 112 can electronically retrieve the data candidate 202 from any suitable user-interface device (not shown) that is integrated with the intelligent protocoling exception system 102. In any case, the receiver component 112 can electronically obtain and/or access the data candidate 202, such that other components of the intelligent protocoling exception system 102 can electronically interact with the data candidate 202.

In various aspects, the data candidate 202 can be any suitable electronic data that pertains to, relates to, and/or is otherwise associated with a medical patient, where it is desired to execute/perform some medical imaging protocol by the medical scanner 104 on the medical patient. In various instances, the data candidate 202 can indicate, represent, and/or otherwise convey any suitable medically-relevant information about the medical patient. For example, in some cases, the data candidate 202 can indicate a pathology, disease, illness, injury, and/or malady with which the medical patient is afflicted and/or for which the medical scanner 104 is desired to be used for purposes of diagnosis and/or prognosis. In various aspects, the data candidate 202 can further indicate any suitable characteristics and/or demographics of the medical patient, such as an age of the medical patient, a sex of the medical patient, a height of the medical patient, a weight of the medical patient, a body composition of the medical patient, a blood type of the medical patient, a heartrate of the medical patient, a breathing rate of the medical patient, a temperature of the medical patient, a surgical history of the medical patient, a disease history of the medical patient, a medication history of the medical patient, a diet of the medical patient, and/or an implant of the medical patient. In various instances, the data candidate 202 can further indicate any other suitable information about the medical patient, such as an identity of a medical professional that is overseeing/treating the medical patient, a location/address of a healthcare facility that is treating the medical patient, and/or a date and/or time at which a scan by the medical scanner 104 is desired/planned to be performed on the medical patient. Further, in some cases, the data candidate 202 can include any suitable information pertaining to the medical scanner 104, such as a hardware version and/or a software version (e.g., a hardware and/or software model year) of the medical scanner 104.

As those having ordinary skill in the art will appreciate, the data candidate 202 can have any suitable format and/or dimensionality as desired. For instance, the data candidate 202 can be one or more scalars, one or more vectors, one or more matrices, one or more tensors, one or more character strings, and/or any suitable combination thereof.

As those having ordinary skill in the art will appreciate, the receiver component 112 can, in some cases, obtain the data candidate 202 from any suitable biometric sensors (not shown) and/or cameras (not shown) that are monitoring in real-time the medical patient.

Figure 3:
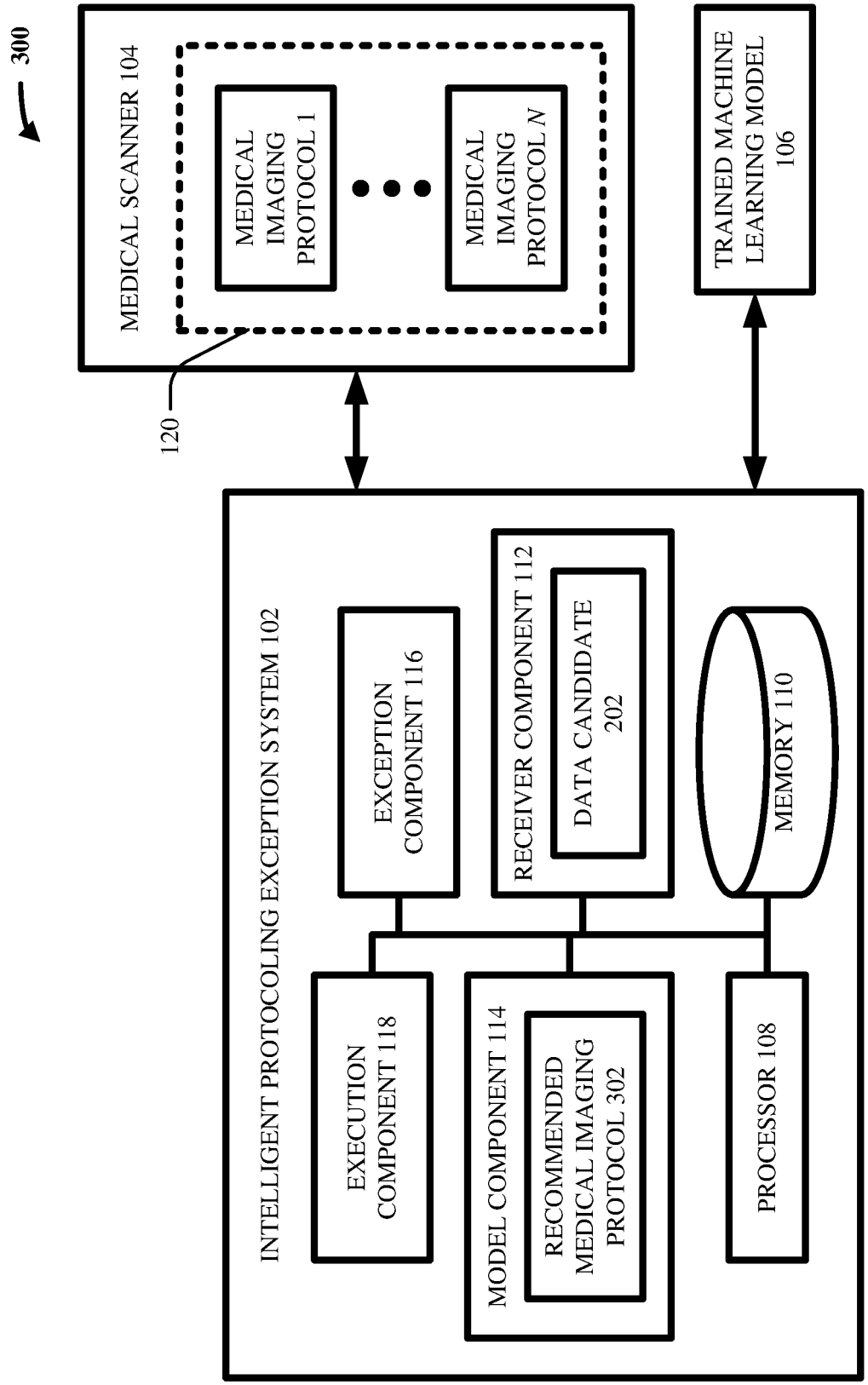
FIG. 3 illustrates a block diagram of an example, non-limiting system including a recommended medical imaging protocol that facilitates customized exceptions to intelligent protocoling in accordance with one or more embodiments described herein.

FIG. 3 illustrates a block diagram of an example, non-limiting system 300 including a recommended medical imaging protocol that can facilitate customized exceptions to intelligent protocoling in accordance with one or more embodiments described herein. As shown, the system 300 can, in some cases, comprise the same components as the system 200, and can further comprise a recommended medical imaging protocol 302.

In various embodiments, the model component 114 can electronically identify the recommended medical imaging protocol 302, by executing the trained machine learning model 106 on the data candidate 202. This is explained more with respect to FIG. 4.

Figure 4:
FIG. 4 illustrates an example, non-limiting block diagram showing how a trained machine learning model can identify a recommended medical imaging protocol in accordance with one or more embodiments described herein.

FIG. 4 illustrates an example, non-limiting block diagram 400 showing how the trained machine learning model 106 can identify the recommended medical imaging protocol 302 in accordance with one or more embodiments described herein.

In various aspects, the model component 114 can electronically execute the trained machine learning model 106 on the data candidate 202 (and/or on any suitable portion and/or subset of the data candidate 202). For example, suppose that the trained machine learning model 106 exhibits a deep learning neural network architecture. In such case, the model component 114 can electronically feed the data candidate 202 (and/or any suitable portion/subset thereof) to an input layer of the trained machine learning model 106. In various instances, the data candidate 202 (and/or any suitable subset/portion thereof) can complete a forward pass through one or more hidden layers of the trained machine learning model 106. Finally, an output layer of the trained machine learning model 106 can compute and/or calculate a classification label based on activation values provided by the one or more hidden layers, where the classification label can indicate and/or represent the recommended medical imaging protocol 302. In any case, the recommended medical imaging protocol 302 can be any one of the set of medical imaging protocols 120. More specifically, the recommended medical imaging protocol 302 can be that particular one of the set of medical imaging protocols 120 which the trained machine learning model 106 believes and/or infers should correspond to the data candidate 202 (e.g., which the trained machine learning model 106 believes and/or infers should be performed on the medical patient).

Although the trained machine learning model 106 can have undergone training (e.g., supervised training), it can nevertheless be possible that the recommended medical imaging protocol 302 is inaccurate and/or incorrect. That is, it can nevertheless be the case that the recommended medical imaging protocol 302 should not be performed on the medical patient that corresponds to the data candidate 202.

Figure 5:
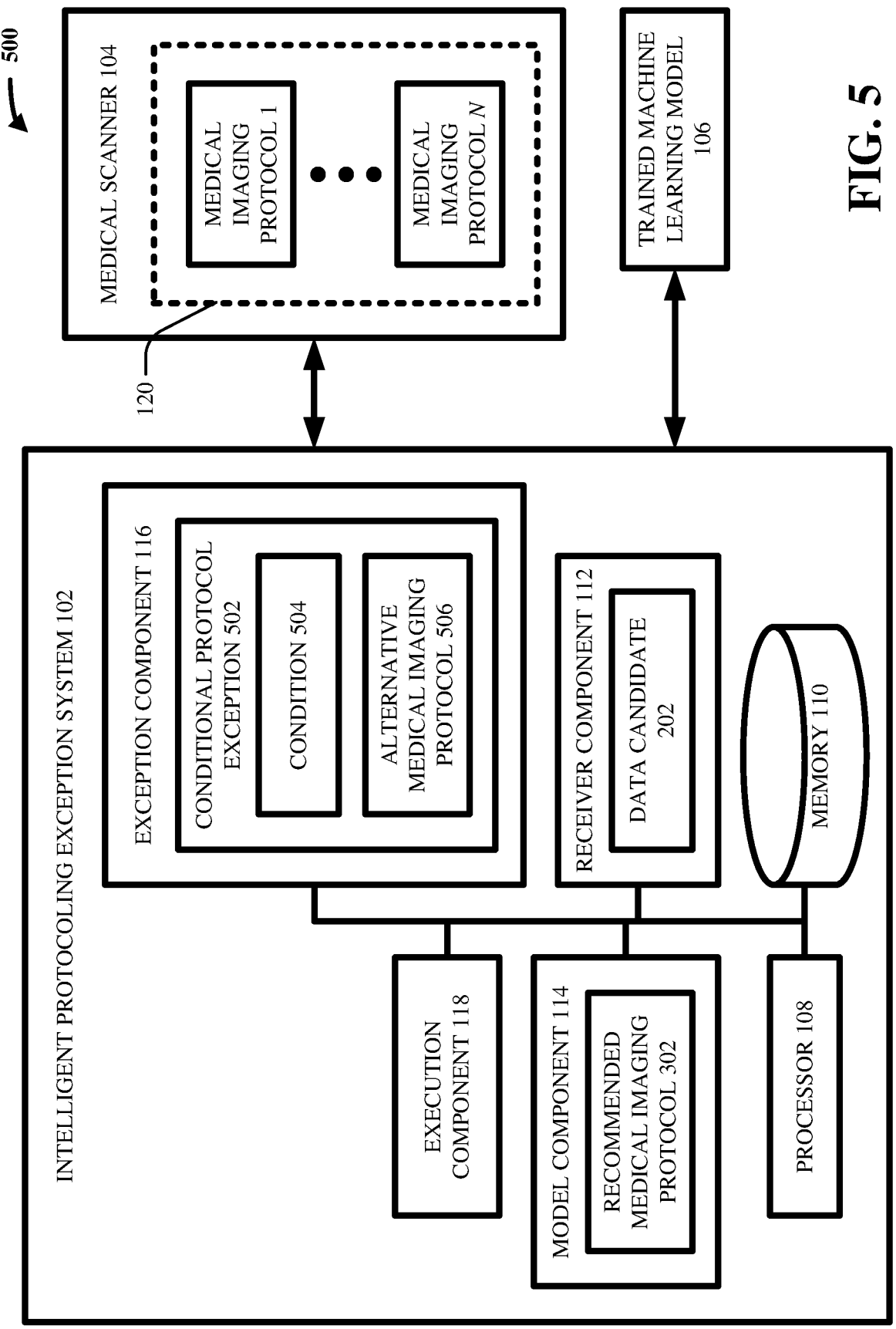
FIG. 5 illustrates a block diagram of an example, non-limiting system including a conditional protocol exception that facilitates customized exceptions to intelligent protocoling in accordance with one or more embodiments described herein.

FIG. 5 illustrates a block diagram of an example, non-limiting system 500 including a conditional protocol exception that can facilitate customized exceptions to intelligent protocoling in accordance with one or more embodiments described herein. As shown, the system 500 can, in some cases, comprise the same components as the system 300, and can further comprise a conditional protocol exception 502.

In various embodiments, the exception component 116 can electronically store, electronically maintain, and/or otherwise electronically access the conditional protocol exception 502. In various aspects, the conditional protocol exception 502 can be any suitable electronic data that indicates, conveys, and/or otherwise represents a condition 504 and/or an alternative medical imaging protocol 506. In various instances, the alternative medical imaging protocol 506 can be any one of the set of medical imaging protocols 120 that is different from the recommended medical imaging protocol 302. In various cases, the condition 504 can be any suitable logical expression that is made up of any suitable Boolean operators (e.g., AND, OR, NOR, NOT) and/or any suitable logical operators (e.g., greater than, less than, equal to, greater than or equal to, less than or equal to, not equal to) that are applicable to the data candidate 202. Accordingly, the condition 504 can, when applied to the data candidate 202, be considered as having a truth value (e.g., as either being true or false). If the data candidate 202 causes the condition 504 to have a true truth value, the data candidate 202 can be considered as satisfying the condition 504 and/or as otherwise triggering the conditional protocol exception 502. On the other hand, if the data candidate 202 causes the condition 504 to have a false truth value, the data candidate 202 can be considered as failing to satisfy the condition 504 and/or as otherwise failing to trigger the conditional protocol exception 502. In any case, the conditional protocol exception 502 can be considered as an electronic instruction and/or an electronic command which calls for the implementation, execution, and/or performance of the alternative medical imaging protocol 506, instead of the recommended medical imaging protocol 302, when the condition 504 is satisfied (e.g., when the condition 504 has a true truth value).

As a non-limiting example, suppose that the data candidate 202 indicates a heartrate of the medical patient and a hardware model year of the medical scanner 104. Furthermore, suppose that the condition 504 indicates that the heartrate of the medical patient is greater than 150 beats per minute and that the hardware model year is 2019 or newer. In various aspects, the exception component 116 can electronically determine what truth value the data candidate 202 causes the condition 504 to have. That is, if the data candidate 202 indicates that the heartrate of the medical patient is indeed greater than 150 beats per minute, and if the data candidate 202 also indicates that the hardware model year of the medical scanner 104 is 2019 or newer, then the exception component 116 can conclude that the condition 504 has a true truth value. In other words, the exception component 116 can conclude that the data candidate 202 satisfies the condition 504. In contrast, if the data candidate 202 instead indicates that the heartrate of the medical patient is not actually greater than 150 beats per minute, or if the data candidate 202 instead indicates that the hardware model year of the medical scanner 104 is not 2019 or newer, then the exception component 116 can conclude that the condition 504 has a false truth value. In other words, the exception component 116 can conclude that the data candidate 202 fails to satisfy the condition 504.

In some cases, the condition 504 can pertain to, relate to, and/or otherwise describe a situation (e.g., a combination and/or permutation of values of the data candidate 202) that was not captured/represented in the data on which the trained machine learning model 106 was trained. In some other cases, the condition 504 can pertain to, relate to, and/or otherwise describe a situation (e.g., a combination and/or permutation of values of the data candidate 202) that was captured/represented in the data on which the trained machine learning model 106 was trained but that was so rare and/or idiosyncratic as to be unable to be confidently learned by the trained machine learning model 106. In still some other cases, the condition 504 can pertain to and/or relate to variables that are unknown and/or otherwise hidden from the trained machine learning model 106. As a non-limiting example, suppose that the data candidate 202 indicates a pathology of the medical patient, a height/weight of the medical patient, a blood type of the medical patient, a breathing rate of the medical patient, and an identifier of a physician attending to the medical patient. Furthermore, suppose that the trained machine learning model 106 is configured to receive as input only a portion of the data candidate 202, which portion indicates the pathology, the height/weight, and the blood type. In such case, the condition 504 can pertain to and/or relate to a remainder of the data candidate 202 which the trained machine learning model 106 is not configured to receive as input, which remainder indicates the breathing rate and/or the physician identifier (e.g., the condition 504 can state that the breathing rate is greater than a specific threshold and/or that the physician identifier is equal to a specific category). Because the trained machine learning model 106 can be not configured to receive as input the remainder of the data candidate 202, and because the condition 504 can pertain to the remainder of the data candidate 202, the condition 504 can be considered as pertaining and/or relating to information and/or variables that are hidden from and/or unknown by the trained machine learning model 106.

In any case, the exception component 116 can electronically determine whether or not the data candidate 202 triggers the conditional protocol exception 502 (e.g., the exception component 116 can apply the condition 504 to the data candidate 202, so as to determine the truth value of the condition 504).

In various embodiments, the execution component 118 can electronically initiate and/or perform any suitable electronic actions based on the determination of the exception component 116. For example, in various aspects, the exception component 116 can determine that the data candidate 202 satisfies and/or triggers the conditional protocol exception 502. In response to such determination, the execution component 118 can electronically implement, execute, and/or auto-select the alternative medical imaging protocol 506 instead of the recommended medical imaging protocol 302. In other words, the execution component 118 can electronically instruct, command, and/or otherwise cause the medical scanner 104 to perform the alternative medical imaging protocol 506 on the medical patient, rather than the recommended medical imaging protocol 302. In some cases, in response to such determination by the exception component 116, the execution component 118 can electronically render, on any suitable computer screen/display (not shown), a list showing and/or depicting the set of medical imaging protocols 120, and the execution component 118 can electronically highlight, embolden, and/or otherwise visually emphasize in such list the alternative medical imaging protocol 506, so as to visually convey (e.g., to a technologist and/or user) that the alternative medical imaging protocol 506 should be manually selected for the medical patient. In still some other cases, in response to such determination by the exception component 116, the execution component 118 can electronically render, on any suitable computer screen/display (not shown), a list showing and/or depicting the set of medical imaging protocols 120, and the execution component 118 can electronically hide, gray-out, and/or otherwise visually deemphasize in such list all but the alternative medical imaging protocol 506, so as to visually convey (e.g., to a technologist and/or user) that the alternative medical imaging protocol 506 should be manually selected for the medical patient.

As another example, in various aspects, the exception component 116 can determine that the data candidate 202 fails to satisfy and/or fails to trigger the conditional protocol exception 502. In response to such determination, the execution component 118 can electronically implement, execute, and/or auto-select the recommended medical imaging protocol 302 instead of the alternative medical imaging protocol 506. In other words, the execution component 118 can electronically instruct, command, and/or otherwise cause the medical scanner 104 to perform the recommended medical imaging protocol 302 on the medical patient, rather than the alternative medical imaging protocol 506. In some cases, in response to such determination by the exception component 116, the execution component 118 can electronically render, on any suitable computer screen/display (not shown), a list showing and/or depicting the set of medical imaging protocols 120, and the execution component 118 can electronically highlight, embolden, and/or otherwise visually emphasize in such list the recommended medical imaging protocol 302, so as to visually convey (e.g., to a technologist and/or user) that the recommended medical imaging protocol 302 should be manually selected for the medical patient. In still some other cases, in response to such determination by the exception component 116, the execution component 118 can electronically render, on any suitable computer screen/display (not shown), a list showing and/or depicting the set of medical imaging protocols 120, and the execution component 118 can electronically hide, gray-out, and/or otherwise visually deemphasize in such list all but the recommended medical imaging protocol 302, so as to visually convey (e.g., to a technologist and/or user) that the recommended medical imaging protocol 302 should be manually selected for the medical patient.

Figure 6:
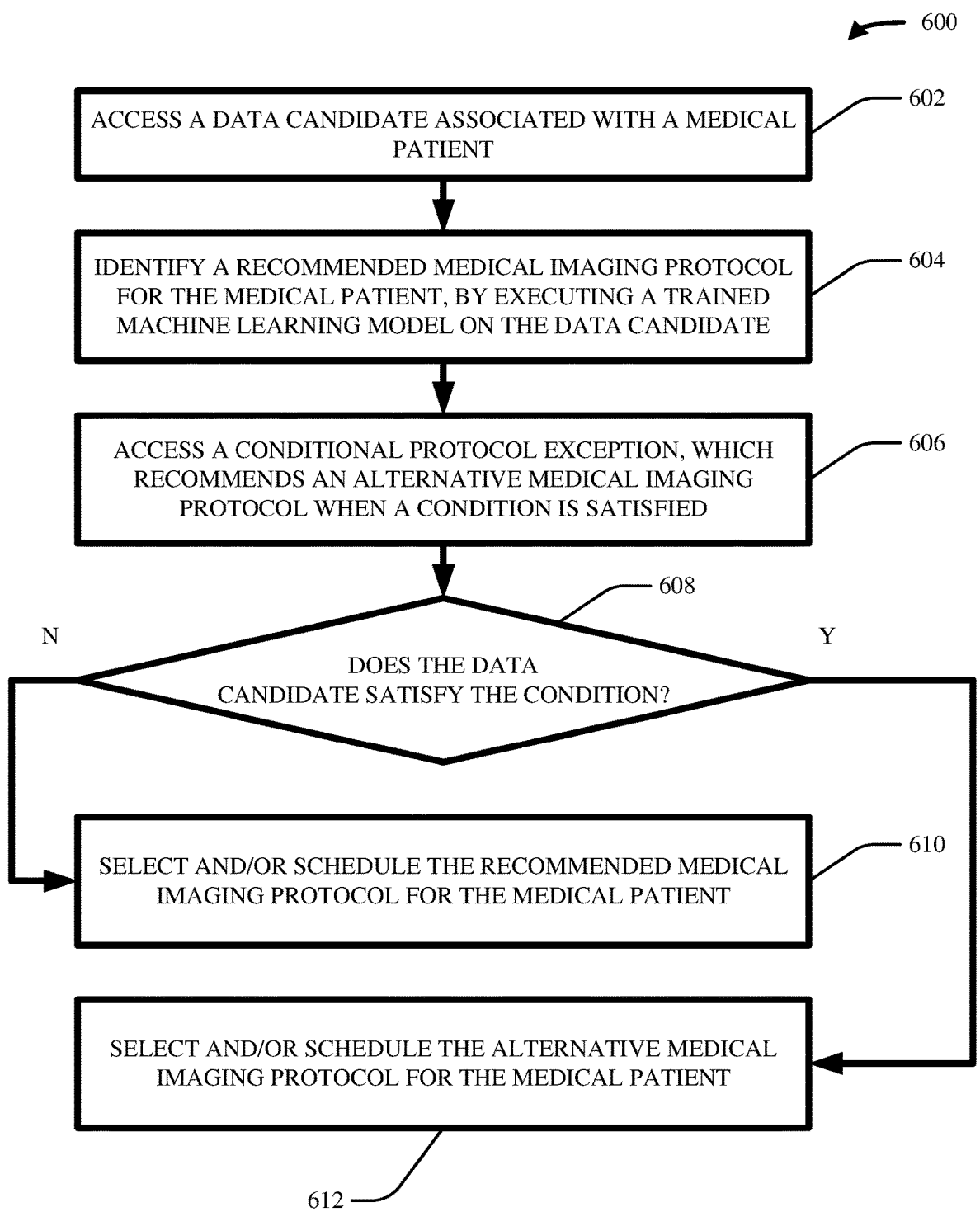
FIG. 6 illustrates a flow diagram of an example, non-limiting computer-implemented method that facilitates customized exceptions to intelligent protocoling in accordance with one or more embodiments described herein.

FIG. 6 illustrates a flow diagram of an example, non-limiting computer-implemented method 600 that can facilitate customized exceptions to intelligent protocoling in accordance with one or more embodiments described herein. In various cases, the intelligent protocoling exception system 102 can facilitate the computer-implemented method 600.

In various embodiments, act 602 can include accessing, by a device (e.g., via 112) operatively coupled to a processor, a data candidate (e.g., 202) associated with a medical patient.

In various aspects, act 604 can include identifying, by the device (e.g., via 114), a recommended medical imaging protocol (e.g., 302) for the medical patient, by executing a trained machine learning model (e.g., 106) on the data candidate.

In various instances, act 606 can include accessing, by the device (e.g., via 116), a conditional protocol exception (e.g., 502), where the conditional protocol exception can recommend and/or call for an alternative medical imaging protocol (e.g., 506) when a condition (e.g., 504) is satisfied.

In various cases, act 608 can include determining, by the device (e.g., via 116), whether the data candidate satisfies the condition. If not, the computer-implemented method 600 can proceed to act 610. If so, the computer-implemented method 600 can proceed to act 612.

In various aspects, act 610 can include selecting and/or scheduling, by the device (e.g., via 118), the recommended medical imaging protocol for the medical patient.

In various instances, act 612 can include selecting and/or scheduling, by the device (e.g., via 118), the alternative medical imaging protocol for the medical patient.

Figure 7:
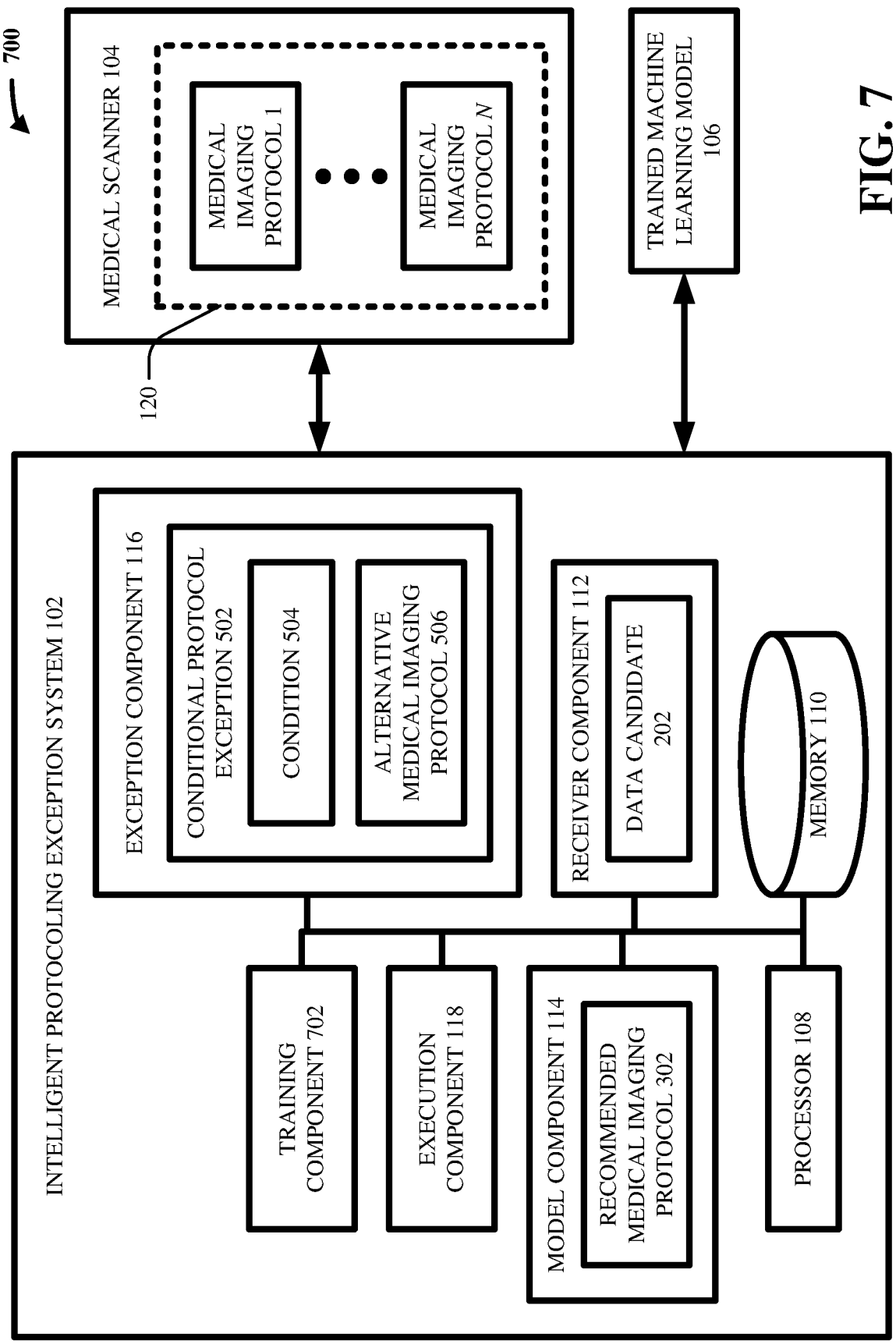
FIG. 7 illustrates a block diagram of an example, non-limiting system including a training component that facilitates customized exceptions to intelligent protocoling in accordance with one or more embodiments described herein.

FIG. 7 illustrates a block diagram of an example, non-limiting system 700 including a training component that can facilitate customized exceptions to intelligent protocoling in accordance with one or more embodiments described herein. As shown, the system 700 can, in some cases, comprise the same components as the system 500, and can further comprise a training component 702.

In various embodiments, when the data candidate 202 satisfies and/or triggers the condition 504, the training component 702 can update and/or overwrite the internal parameters of the trained machine learning model 106 based on the alternative medical imaging protocol 506. This is explained more with respect to FIG. 8.

Figure 8:
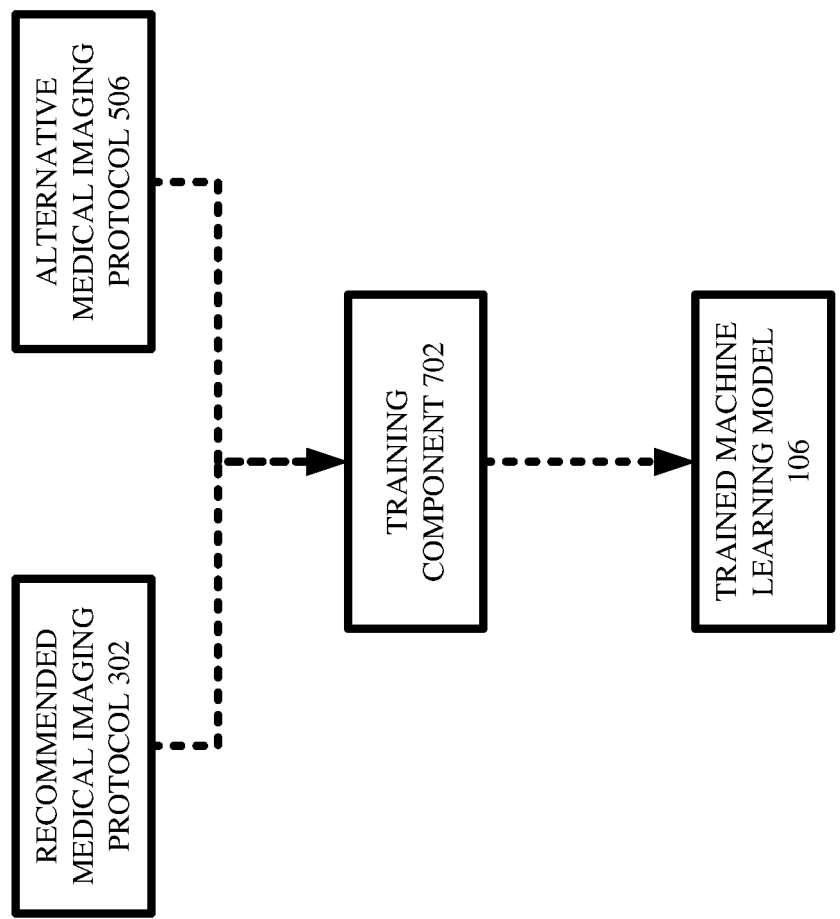
FIG. 8 illustrates an example, non-limiting block diagram showing how a training component can retrain and/or update a trained machine learning model in accordance with one or more embodiments described herein.

FIG. 8 illustrates an example, non-limiting block diagram 800 showing how the training component 702 can retrain and/or update the trained machine learning model 106 in accordance with one or more embodiments described herein.

As explained herein, the trained machine learning model 106 can, in some cases, be considered as an artificial intelligence classifier that can receive as input a data candidate pertaining to a given medical patient and that can produce as output a classification label that indicates which medical imaging protocol should be implemented for that given medical patient. For instance, and as mentioned above, an input layer of the trained machine learning model 106 can receive as input the data candidate 202 (and/or a portion thereof), the data candidate 202 (and/or a portion thereof) can complete a forward pass through one or more hidden layers of the trained machine learning model 106, and/or an output layer of the trained machine learning model 106 can compute a classification label based on activation maps of the one or more hidden layers, where the classification label can indicate and/or identify the recommended medical imaging protocol 302. In such case, the trained machine learning model 106 can be considered as believing and/or inferring that the recommended medical imaging protocol 302 is warranted when given the data candidate 202.

If the exception component 116 determines that the data candidate 202 satisfies/triggers the conditional protocol exception 502, then the recommended medical imaging protocol 302 can be considered as incorrect and/or inaccurate. In other words, if the data candidate 202 causes the condition 504 to have a true truth value, then it can, in some cases, be inferred that the trained machine learning model 106 was incorrect and/or wrong to suggest the recommended medical imaging protocol 302. In such case, the alternative medical imaging protocol 506 can instead be considered as the correct and/or accurate protocol when given the data candidate 202. Accordingly, in various aspects, the training component 702 can treat the alternative medical imaging protocol 506 as a ground-truth annotation that can be leveraged for improving, updating, and/or otherwise overwriting the learned behavior of the trained machine learning model 106. More specifically, in such case, the training component 702 can compute an error and/or loss between the classification label outputted by the trained machine learning model 106 indicating the recommended medical imaging protocol 302 and a classification label indicating the alternative medical imaging protocol 506. In various instances, the training component 702 can perform backpropagation on the internal parameters (e.g., weight values, bias values) of the trained machine learning model 106, where such backpropagation can be driven by the computed error and/or loss. In this way, the training component 702 can help to improve the trained machine learning model 106.

In various embodiments, the conditional protocol exception 502 can be manually defined and/or manually-inputted by a technologist, user, and/or operator via any suitable user-interface device (not shown). Non-limiting examples of such a user-interface device can include keyboards, keypads, touch screens, joysticks, and/or voice controls.

In various other embodiments, the conditional protocol exception 502 can be automatically generated by the exception component 116 based on previous manual overrides experienced by the trained machine learning model 106. This is explained more with respect to FIGS. 9-10.

Figure 9:
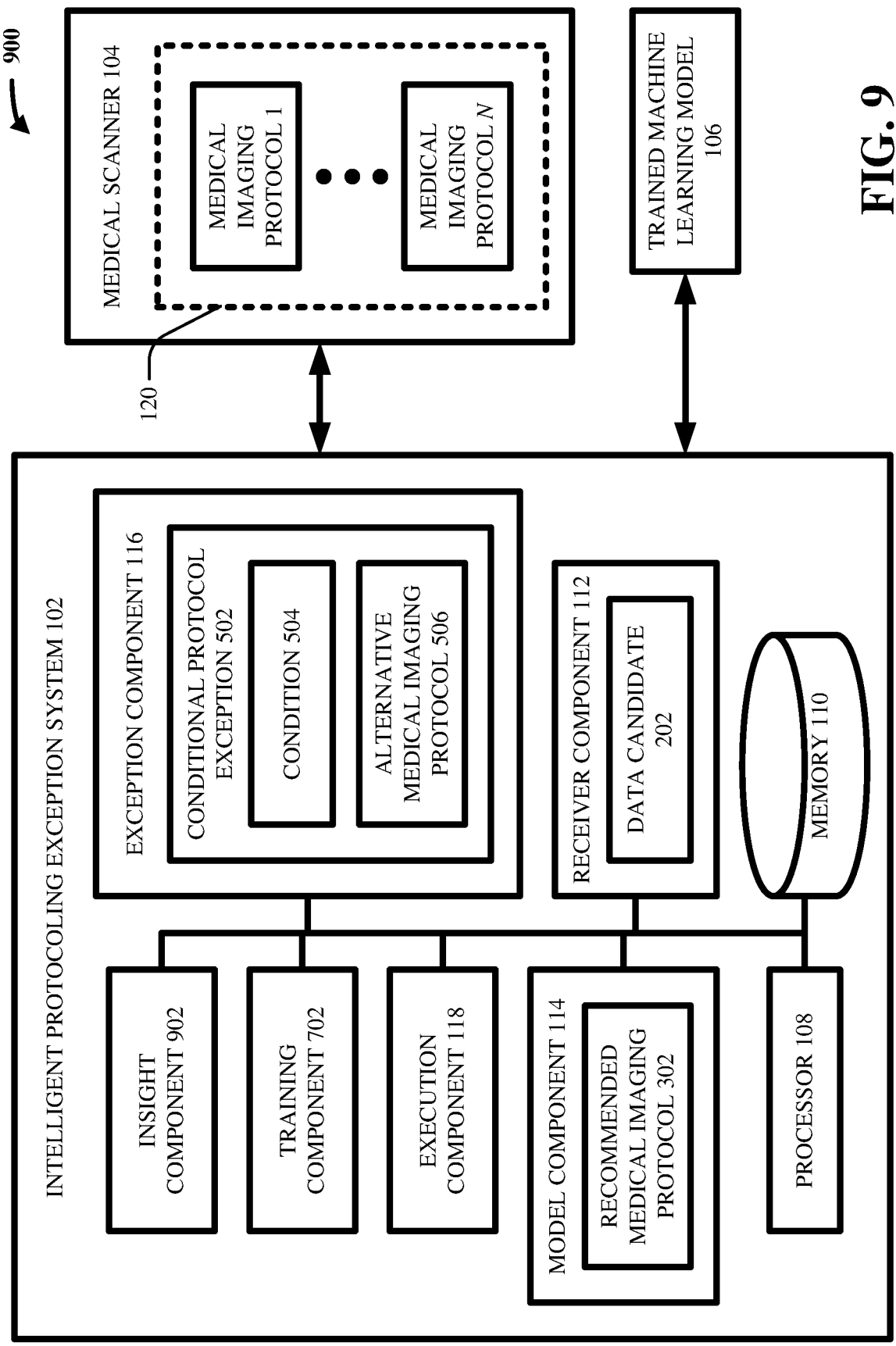
FIG. 9 illustrates a block diagram of an example, non-limiting system including an insight component that facilitates customized exceptions to intelligent protocoling in accordance with one or more embodiments described herein.

FIG. 9 illustrates a block diagram of an example, non-limiting system 900 including an insight component that can facilitate customized exceptions to intelligent protocoling in accordance with one or more embodiments described herein. As shown, the system 900 can, in some cases, comprise the same components as the system 700, and can further comprise an insight component 902.

In various aspects, as described herein, the execution component 118 can refrain from automatically selecting/executing the medical imaging protocols on the medical scanner 104. Instead, in various instances, the execution component 118 can visually render the list of medical imaging protocols 120 on any suitable screen/monitor, and a medical professional and/or technologist that is operating the medical scanner 104 can manually select, via any suitable user-interface device, which of the set of medical imaging protocols 120 to execute. Accordingly, it is possible, in various cases, for the trained machine learning model 106 to make recommendations to the technologist and for the technologist to ignore and/or act contrary to such recommendations. That is, the trained machine learning model 106 can recommend specific medical imaging protocols to the technologist, and the technologist can choose to execute various medical imaging protocols that were not recommended by the trained machine learning model 106. In various aspects, the insight component 902 can electronically track, electronically log, and/or otherwise electronically record such selections by the technologist, and the exception component 116 can electronically analyze such logs/records to generate and/or suggest conditional protocol exceptions. This is explained more with respect to FIG. 10.

Figure 10:
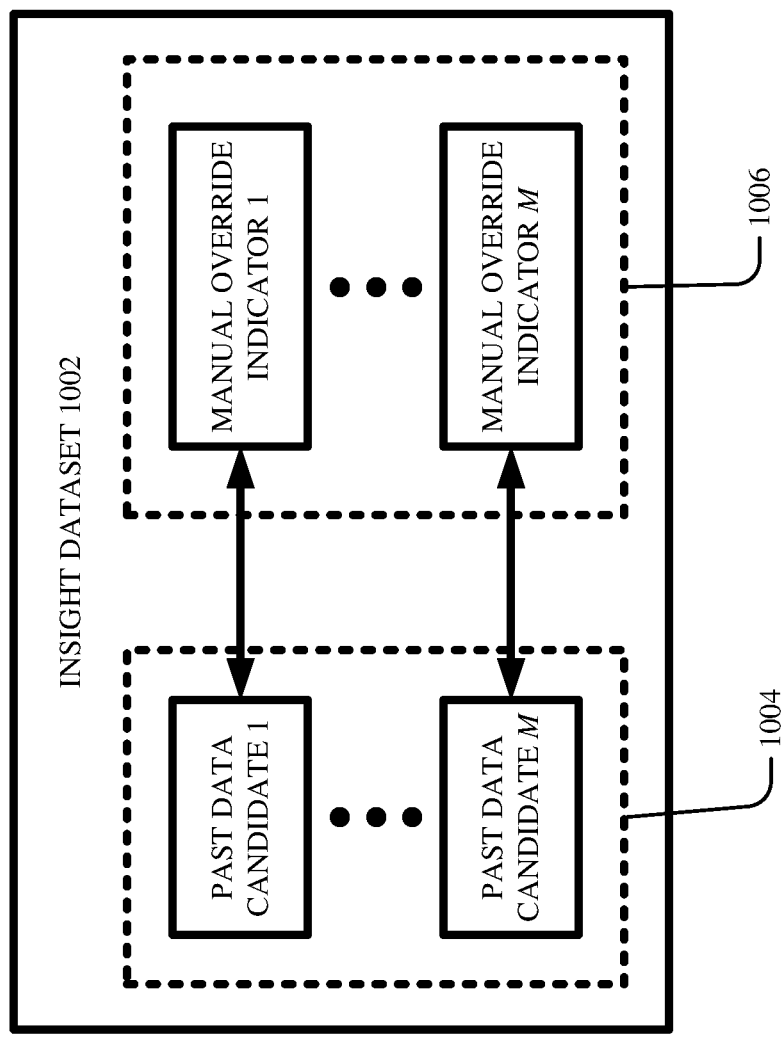
FIG. 10 illustrates an example, non-limiting block diagram of an insight dataset in accordance with one or more embodiments described herein.

FIG. 10 illustrates an example, non-limiting block diagram 1000 of an insight dataset in accordance with one or more embodiments described herein.

In various embodiments, the insight component 902 can electronically record an insight dataset 1002 over time. As shown, the insight dataset 1002 can include a set of past data candidates 1004 and/or a set of manual override indicators 1006 that can respectively correspond to the set of past data candidates 1004. In various instances, the set of past data candidates 1004 can include m data candidates for any suitable positive integer m: a past data candidate 1 to a past data candidate m. Because the set of manual override indicators 1006 can respectively correspond (e.g., in oneto-one fashion) to the set of past data candidates, the set of manual override indicators 1006 can include m indicators: a manual override indicator 1 to a manual override indicator m.

In various cases, the past data candidate 1 can correspond to the manual override indicator 1. In various aspects, the past data candidate 1 can have the same format and/or dimensionality as the data candidate 202 and can have been encountered by the intelligent protocoling exception system 102 at some point in the past. That is, at some point in the past, the receiver component 112 can have accessed the past data candidate 1, and the model component 114 can have executed the trained machine learning model 106 on the past data candidate 1 so as to identify a past medical imaging protocol recommended by the trained machine learning model 106 for the past data candidate 1. Furthermore, a technologist can have, at some point in the past, chosen to either follow the recommendation of the trained machine learning model 106 with respect to the past data candidate 1 or to not follow the recommendation of the trained machine learning model 106 with respect to the past data candidate 1. In various instances, the manual override indicator 1 can be any suitable electronic data, having any suitable format/dimensionality, that indicates and/or otherwise conveys whether the technologist followed or ignored the recommendation of the trained machine learning model 106 with respect to the past data candidate 1. For example, the manual override indicator 1 can indicate both the medical imaging protocol that was recommended by the trained machine learning model 106 for the past data candidate 1 and the medical imaging protocol that was manually selected by the technologist for the past data candidate 1. If the technologist manually selected the protocol that was recommended by the trained machine learning model 106, the manual override indicator 1 can be considered as indicating that the trained machine learning model 106 was not overridden by the technologist. In contrast, if the technologist manually selected a protocol other than the one recommended by the trained machine learning model 106, the manual override indicator 1 can be considered as indicating that the trained machine learning model 106 was overridden by the technologist.

Likewise, the past data candidate m can correspond to the manual override indicator m. In various aspects, the past data candidate m can have the same format and/or dimensionality as the data candidate 202 and can have been encountered by the intelligent protocoling exception system 102 at some point in the past. That is, at some point in the past, the receiver component 112 can have accessed the past data candidate m, and the model component 114 can have executed the trained machine learning model 106 on the past data candidate m so as to identify a past medical imaging protocol recommended by the trained machine learning model 106 for the past data candidate m. Furthermore, a technologist can have, at some point in the past, chosen to either follow or ignore such recommendation. In various instances, just as above, the manual override indicator m can be any suitable electronic data, having any suitable format/dimensionality, that indicates and/or otherwise conveys whether the technologist followed or ignored the recommendation of the trained machine learning model 106 with respect to the past data candidate m.

In any case, the insight component 902 can electronically generate the insight dataset 1002 by recording, logging, and/or tracking the activity of the intelligent protocoling exception system 102 over any suitable period of time, and the exception component 116 can electronically analyze the insight dataset 1002 to generate the conditional protocol exception 502. More specifically, the exception component 116 can electronically apply any suitable statistical techniques (e.g., averaging, clustering, comparison of computed percentages to threshold levels) to the insight dataset 1002 so as to automatically generate the conditional protocol exception 502.

As a non-limiting example, suppose that some subset of the set of past data candidates 1004 indicate a software model year for the medical scanner 104 of 1999 or older. Furthermore, for purposes of this non-limiting example, assume a threshold percentage of x %, for any suitable positive number x between 0 and 100 inclusively, for the creation/generation of a new conditional protocol exception. In various aspects, the exception component 116 can statistically analyze such subset of the set of past data candidates 1004 to determine whether or not such subset merits a new conditional protocol exception. For instance, if the exception component 116 determines that a medical imaging protocol Y was manually selected for at least x % of such subset of past data candidates, then the exception component 116 can electronically generate (and/or can electronically suggest the generation of) a new conditional protocol exception that states the following: implement the medical imaging protocol Y when/if the software model year is 1999 or older. As another non-limiting example, suppose that some other subset of the set of past data candidates 1004 indicate a physician identifier of Dr. Jane Doe. If the exception component 116 determines that a medical imaging protocol Z was manually selected for at least x % of such subset of past data candidates, then the exception component 116 can electronically generate (and/or can electronically suggest the generation of) a new conditional protocol exception that states the following: implement the medical imaging protocol Z when/if the physician identifier is Dr. Jane Doe.

In this way, the exception component 116 can electronically generate the conditional protocol exception 502 based on the insight dataset 1002.

Figure 11:
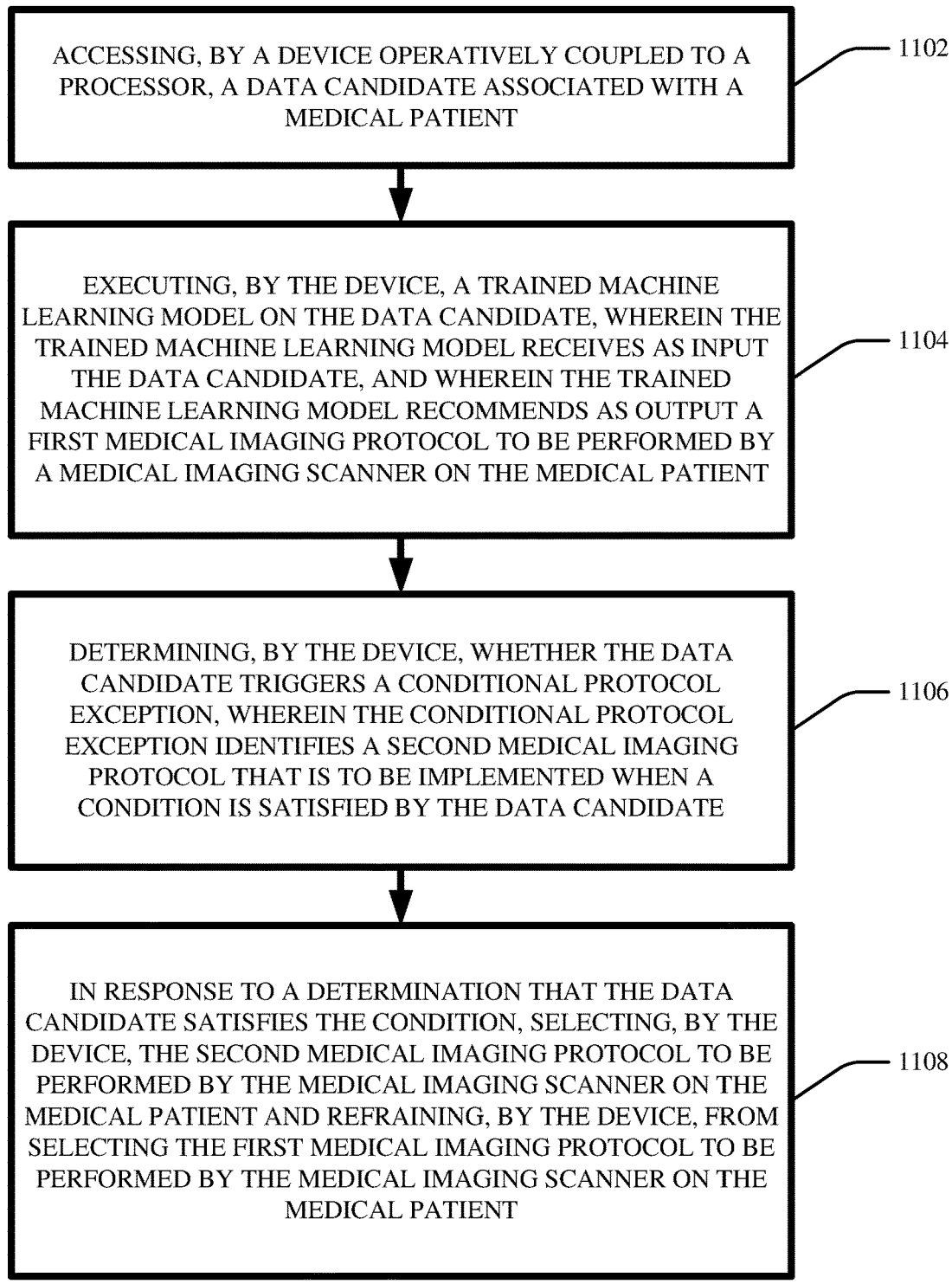
FIG. 11 illustrates a flow diagram of an example, non-limiting computer-implemented method that facilitates customized exceptions to intelligent protocoling in accordance with one or more embodiments described herein.

FIG. 11 illustrates a flow diagram of an example, non-limiting computer-implemented method 1100 that can facilitate customized exceptions to intelligent protocoling in accordance with one or more embodiments described herein. In various cases, the intelligent protocoling exception system 102 can facilitate the computer-implemented method 1100.

In various embodiments, act 1102 can include accessing, by a device (e.g., via 112) operatively coupled to a processor, a data candidate (e.g., 202) associated with a medical patient.

In various aspects, act 1104 can include executing, by the device (e.g., via 114), a trained machine learning model (e.g., 106) on the data candidate. In various cases, the trained machine learning model can receive as input the data candidate, and the trained machine learning model can recommend as output a first medical imaging protocol (e.g., 302) to be performed by a medical imaging scanner (e.g., 104) on the medical patient.

In various instances, act 1106 can include determining, by the device (e.g., via 116), whether the data candidate triggers a conditional protocol exception (e.g., 502). In various cases, the conditional protocol exception can identify a second medical imaging protocol (e.g., 506) that is to be implemented when a condition (e.g., 504) is satisfied by the data candidate.

In various aspects, act 1108 can include, in response to a determination that the data candidate satisfies the condition, selecting, by the device (e.g., via 118), the second medical imaging protocol to be performed by the medical imaging scanner on the medical patient and refraining, by the device (e.g., via 118), from selecting the first medical imaging protocol to be performed by the medical imaging scanner on the medical patient.

Although not explicitly shown in FIG. 11, the computer-implemented method 1100 can further include: in response to a determination that the data candidate fails to satisfy the condition, selecting, by the device (e.g., via 118), the first medical imaging protocol to be performed by the medical imaging scanner on the medical patient and refraining, by the device (e.g., via 118), from selecting the second medical imaging protocol to be performed by the medical imaging scanner on the medical patient.

Although not explicitly shown in FIG. 11, the computer-implemented method 1100 can further include: retraining, by the device (e.g., via 702), the trained machine learning model in a supervised fashion based on the data candidate and the second medical imaging protocol, when the data candidate satisfies the condition (e.g., as shown with respect to FIG. 8).

Although not explicitly shown in FIG. 11, the data candidate can include a medical history of the medical patient, an image or video depicting the medical patient, and/or data produced by at least one real-time biometric sensor affixed to the medical patient.

Although not explicitly shown in FIG. 11, the conditional protocol exception can be a Boolean expression.

Although not explicitly shown in FIG. 11, the conditional protocol exception can be user-defined.

Although not explicitly shown in FIG. 11, the computer-implemented method 1100 can further include: generating, by the device (e.g., via 116 and/or 902), the conditional protocol exception based on a statistical analysis of previous manual overrides (e.g., 1002, 1004, and/or 1006) of the trained machine learning model.

Accordingly, various embodiments described herein can be considered as a computerized tool that can leverage conditional protocol exceptions so as to handle and/or catch situations in which an intelligent protocoling model is likely to incorrectly recommend a medical imaging protocol. Such a computerized tool is certainly a useful and practical application of computers.

Although the herein disclosure mainly describes various embodiments as implementing a single conditional protocol exception (e.g., 502), this is a mere non-limiting example for ease of explanation and illustration. Those having ordinary skill in the art will appreciate that any suitable number of conditional protocol exceptions can be implemented as desired.

In various instances, machine learning algorithms and/or models can be implemented in any suitable way to facilitate any suitable aspects described herein. To facilitate some of the above-described machine learning aspects of various embodiments of the subject innovation, consider the following discussion of artificial intelligence (AI). Various embodiments of the present innovation herein can employ artificial intelligence to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, z_n)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Those having ordinary skill in the art will appreciate that the herein disclosure describes non-limiting examples of various embodiments of the subject innovation. For ease of description and/or explanation, various portions of the herein disclosure utilize the term "each" when discussing various embodiments of the subject innovation. Those having ordinary skill in the art will appreciate that such usages of the term "each" are non-limiting examples. In other words, when the herein disclosure provides a description that is applied to "each" of some particular object and/or component, it should be understood that this is a non-limiting example of various embodiments of the subject innovation, and it should be further understood that, in various other embodiments of the subject innovation, it can be the case that such description applies to fewer than "each" of that particular object and/or component.

Figure 12:
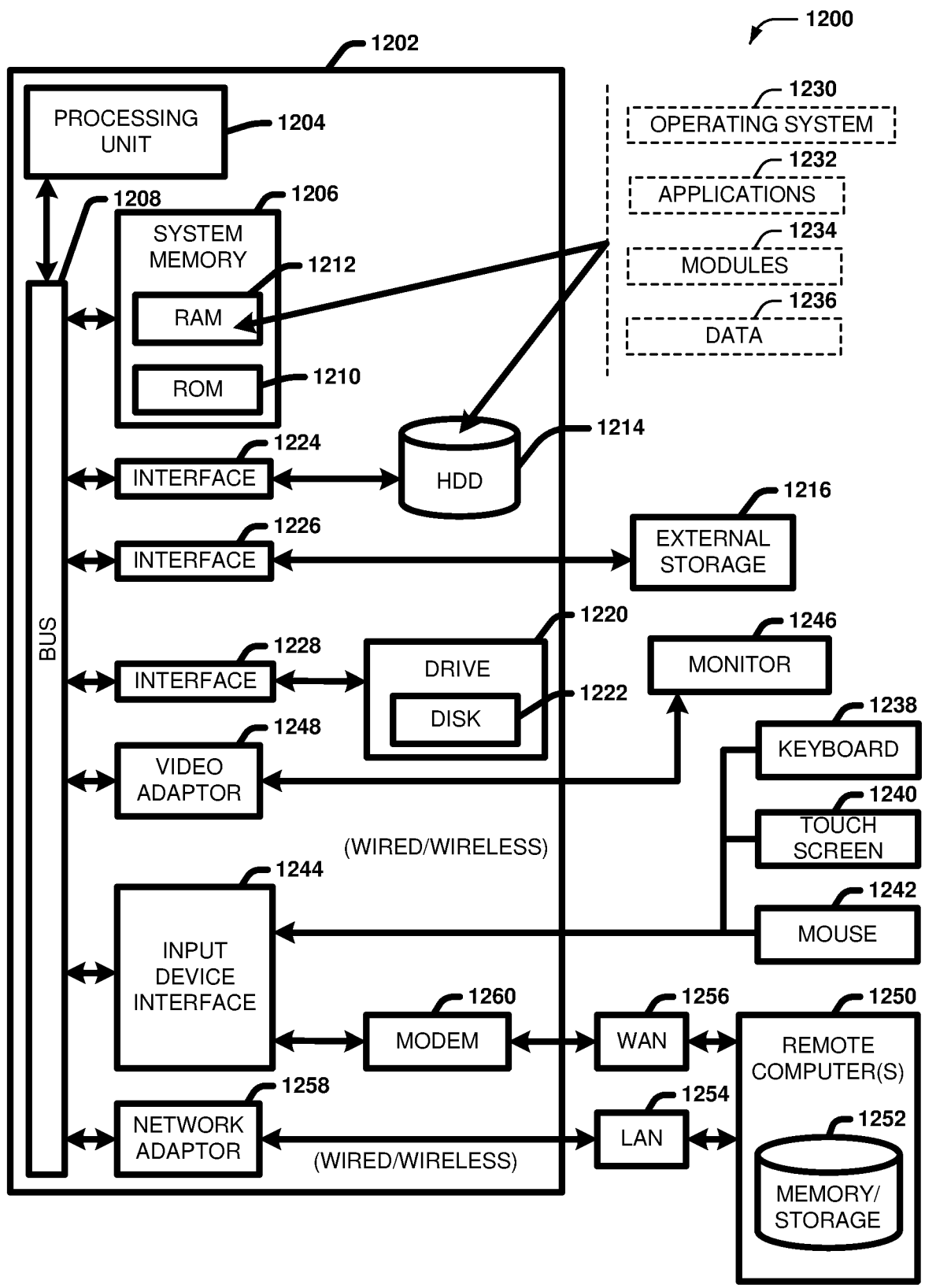
FIG. 12 illustrates a block diagram of an example, non-limiting operating environment in which one or more embodiments described herein can be facilitated.

In order to provide additional context for various embodiments described herein, FIG. 12 and the following discussion are intended to provide a brief, general description of a suitable computing environment 1200 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, the example environment 1200 for implementing various embodiments of the aspects described herein includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors. Dual microprocessors and other multi-processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes ROM 1210 and RAM 1212. A basic input/output system (BIOS) can be stored in a non-volatile memory such as ROM, erasable programmable read only memory (EPROM), EEPROM, which BIOS contains the basic routines that help to transfer information between elements within the computer 1202, such as during startup. The RAM 1212 can also include a high-speed RAM such as static RAM for caching data.

The computer 1202 further includes an internal hard disk drive (HDD) 1214 (e.g., EIDE, SATA), one or more external storage devices 1216 (e.g., a magnetic floppy disk drive (FDD) 1216, a memory stick or flash drive reader, a memory card reader, etc.) and a drive 1220, e.g., such as a solid state drive, an optical disk drive, which can read or write from a disk 1222, such as a CD-ROM disc, a DVD, a BD, etc. Alternatively, where a solid state drive is involved, disk 1222 would not be included, unless separate. While the internal HDD 1214 is illustrated as located within the computer 1202, the internal HDD 1214 can also be configured for external use in a suitable chassis (not shown). Additionally, while not shown in environment 1200, a solid state drive (SSD) could be used in addition to, or in place of, an HDD 1214. The HDD 1214, external storage device(s) 1216 and drive 1220 can be connected to the system bus 1208 by an HDD interface 1224, an external storage interface 1226 and a drive interface 1228, respectively. The interface 1224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1212, including an operating system 1230, one or more application programs 1232, other program modules 1234 and program data 1236. All or portions of the operating system, applications, modules, and/or data can also be cached in the RAM 1212. The systems and methods described herein can be implemented utilizing various commercially available operating systems or combinations of operating systems.

Computer 1202 can optionally comprise emulation technologies. For example, a hypervisor (not shown) or other intermediary can emulate a hardware environment for operating system 1230, and the emulated hardware can optionally be different from the hardware illustrated in FIG. 12. In such an embodiment, operating system 1230 can comprise one virtual machine (VM) of multiple VMs hosted at computer 1202. Furthermore, operating system 1230 can provide runtime environments, such as the Java runtime environment or the .NET framework, for applications 1232. Runtime environments are consistent execution environments that allow applications 1232 to run on any operating system that includes the runtime environment. Similarly, operating system 1230 can support containers, and applications 1232 can be in the form of containers, which are lightweight, standalone, executable packages of software that include, e.g., code, runtime, system tools, system libraries and settings for an application.

Further, computer 1202 can be enable with a security module, such as a trusted processing module (TPM). For instance with a TPM, boot components hash next in time boot components, and wait for a match of results to secured values, before loading a next boot component. This process can take place at any layer in the code execution stack of computer 1202, e.g., applied at the application execution level or at the operating system (OS) kernel level, thereby enabling security at any level of code execution.

A user can enter commands and information into the computer 1202 through one or more wired/wireless input devices, e.g., a keyboard 1238, a touch screen 1240, and a pointing device, such as a mouse 1242. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1204 through an input device interface 1244 that can be coupled to the system bus 1208, but can be connected by other interfaces, such as a parallel port, an IEEE 1394 serial port, a game port, a USB port, an IR interface, a BLUETOOTH® interface, etc.

A monitor 1246 or other type of display device can be also connected to the system bus 1208 via an interface, such as a video adapter 1248. In addition to the monitor 1246, a computer typically includes other peripheral output devices (not shown), such as speakers, printers, etc.

The computer 1202 can operate in a networked environment using logical connections via wired and/or wireless communications to one or more remote computers, such as a remote computer(s) 1250. The remote computer(s) 1250 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1252 is illustrated. The logical connections depicted include wired/wireless connectivity to a local area network (LAN) 1254 and/or larger networks, e.g., a wide area network (WAN) 1256. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 can be connected to the local network 1254 through a wired and/or wireless communication network interface or adapter 1258. The adapter 1258 can facilitate wired or wireless communication to the LAN 1254, which can also include a wireless access point (AP) disposed thereon for communicating with the adapter 1258 in a wireless mode.

When used in a WAN networking environment, the computer 1202 can include a modem 1260 or can be connected to a communications server on the WAN 1256 via other means for establishing communications over the WAN 1256, such as by way of the Internet. The modem 1260, which can be internal or external and a wired or wireless device, can be connected to the system bus 1208 via the input device interface 1244. In a networked environment, program modules depicted relative to the computer 1202 or portions thereof, can be stored in the remote memory/storage device 1252. It will be appreciated that the network connections shown are example and other means of establishing a communications link between the computers can be used.

When used in either a LAN or WAN networking environment, the computer 1202 can access cloud storage systems or other network-based storage systems in addition to, or in place of, external storage devices 1216 as described above, such as but not limited to a network virtual machine providing one or more aspects of storage or processing of information. Generally, a connection between the computer 1202 and a cloud storage system can be established over a LAN 1254 or WAN 1256 e.g., by the adapter 1258 or modem 1260, respectively. Upon connecting the computer 1202 to an associated cloud storage system, the external storage interface 1226 can, with the aid of the adapter 1258 and/or modem 1260, manage storage provided by the cloud storage system as it would other types of external storage. For instance, the external storage interface 1226 can be configured to provide access to cloud storage sources as if those sources were physically connected to the computer 1202.

The computer 1202 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 13:
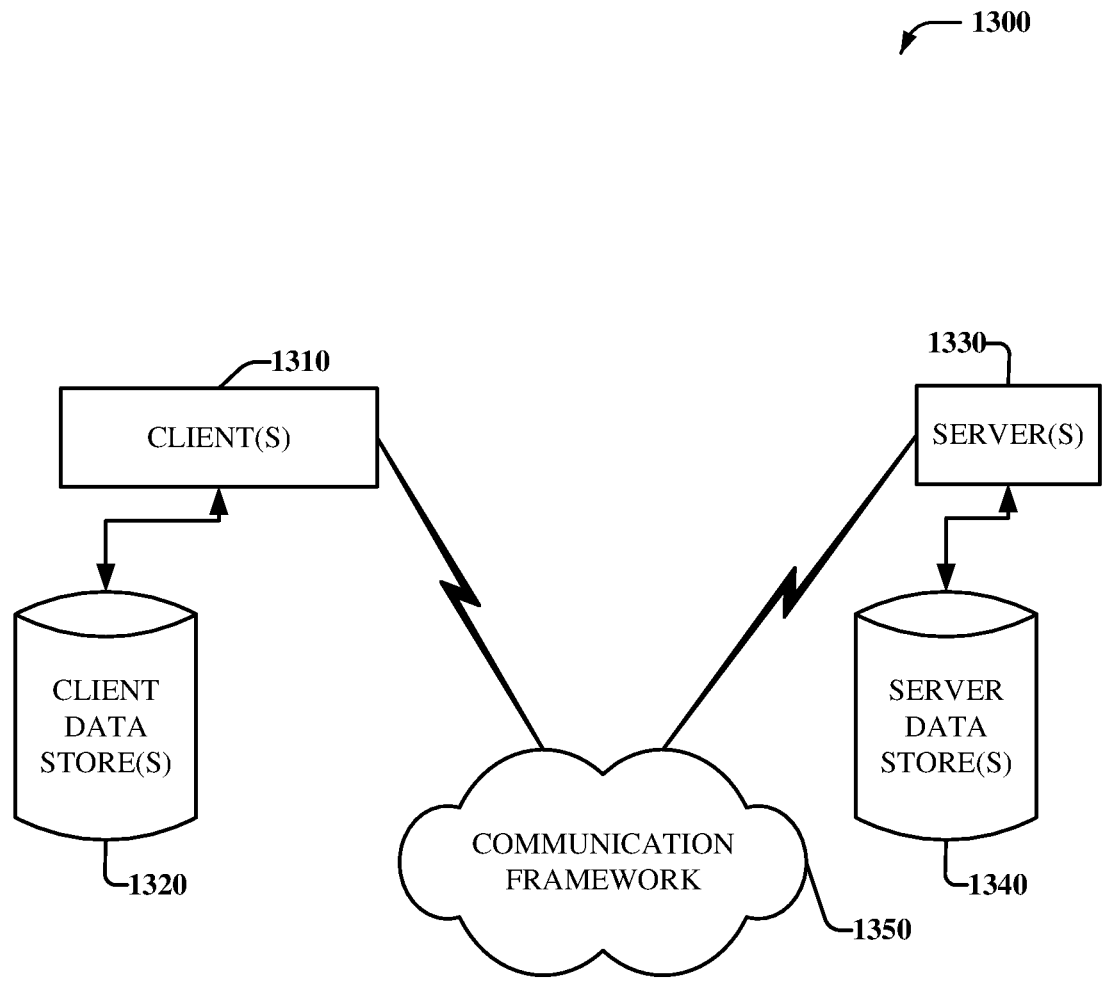
FIG. 13 illustrates an example networking environment operable to execute various implementations described herein.

FIG. 13 is a schematic block diagram of a sample computing environment 1300 with which the disclosed subject matter can interact. The sample computing environment 1300 includes one or more client(s) 1310. The client(s) 1310 can be hardware and/or software (e.g., threads, processes, computing devices). The sample computing environment 1300 also includes one or more server(s) 1330. The server(s) 1330 can also be hardware and/or software (e.g., threads, processes, computing devices). The servers 1330 can house threads to perform transformations by employing one or more embodiments as described herein, for example. One possible communication between a client 1310 and a server 1330 can be in the form of a data packet adapted to be transmitted between two or more computer processes. The sample computing environment 1300 includes a communication framework 1350 that can be employed to facilitate communications between the client(s) 1310 and the server(s) 1330. The client(s) 1310 are operably connected to one or more client data store(s) 1320 that can be employed to store information local to the client(s) 1310. Similarly, the server (s) 1330 are operably connected to one or more server data store(s) 1340 that can be employed to store information local to the servers 1330.

Various embodiments described herein may be a system, a method, an apparatus and/or a computer program product at any possible technical detail level of integration. The computer program product can include a computer readable storage medium (or media) having computer readable program instructions thereon for causing a processor to carry out aspects of various embodiments described herein. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments described herein can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of various embodiments described herein.

Aspects of various embodiments are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function (s). In some alternative implementations, the functions noted in the blocks can occur out of the order noted in the Figures.

For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a processor that executes computer-executable components stored in a computer-readable memory, the computer-executable components comprising:
   a receiver component that accesses a data candidate associated with a medical patient;
   a model component that executes a trained intelligent protocoling classifier on the data candidate, wherein the trained intelligent protocoling classifier receives as input a portion of the data candidate and does not receive as input a remainder of the data candidate, wherein the trained intelligent protocoling classifier produces as output a classification label, and wherein the classification label indicates a first medical imaging protocol to be performed by a medical imaging scanner on the medical patient;
   an exception component that computes a truth value of a logical Boolean expression, by applying the logical Boolean expression to the remainder of the data candidate and not to the portion of the data candidate, wherein the logical Boolean expression corresponds to a second medical imaging protocol that is different from the first medical imaging protocol; and
   an execution component that, in response to the exception component computing a true truth value of the logical Boolean expression, causes the medical imaging scanner to perform the second medical imaging protocol on the medical patient rather than the first medical imaging protocol.

2. The system of claim 1, wherein the execution component, in response to the exception component computing a false truth value of the logical Boolean expression, causes the medical imaging scanner to perform the first medical imaging protocol on the medical patient rather than the second medical imaging protocol.

3. The system of claim 1, wherein the computer-executable components further comprise:
   a training component that retrains the trained intelligent protocoling classifier by treating the data candidate as a training input and by treating the second medical imaging protocol as a ground-truth classification label, in response to the exception component computing the true truth value of the logical Boolean expression.

4. The system of claim 1, wherein the portion of the data candidate includes a medical history of the medical patient, an image or video depicting the medical patient, or data produced by at least one real-time biometric sensor affixed to the medical patient.

5. The system of claim 1, wherein the remainder of the data candidate includes: a physician identifier associated with the medical patient; a time at which scanning of the medical patient is desired; or a hardware or software version identifier associated with the medical imaging scanner.

6. The system of claim 1, wherein the logical Boolean expression is user-defined.

7. The system of claim 1, wherein the exception component generates the logical Boolean expression based on a statistical analysis of previous manual overrides of the trained intelligent protocoling classifier.

8. A computer-implemented method, comprising:
   accessing, by a device operatively coupled to a processor, a data candidate associated with a medical patient;
   executing, by the device, a trained intelligent protocoling classifier on the data candidate, wherein the trained intelligent protocoling classifier receives as input a portion of the data candidate and does not receive as input a remainder of the data candidate, wherein the trained intelligent protocoling classifier produces as output a classification label, and wherein the classification label indicates a first medical imaging protocol to be performed by a medical imaging scanner on the medical patient;
   computing, by the device, a truth value of a logical Boolean expression, by applying the logical Boolean expression to the remainder of the data candidate and not to the portion of the data candidate, wherein the logical Boolean expression corresponds to a second medical imaging protocol that is different from the first medical imaging protocol; and
   in response to computation of a true truth value of the logical Boolean expression, causing, by the device, the medical imaging scanner to perform the second medical imaging protocol on the medical patient rather than the first medical imaging protocol.

9. The computer-implemented method of claim 8, further comprising:
   in response to computation of a false truth value of the logical Boolean expression, causing, by the device, the medical imaging scanner to perform the first medical imaging protocol on the medical patient rather than the second medical imaging protocol.

10. The computer-implemented method of claim 8, further comprising:
    retraining, by the device, the trained intelligent protocol classifier by treating the data candidate as a training input and by treating the second medical imaging protocol as a ground-truth classification label, in response to the computation of the true truth value of the logical Boolean expression.

11. The computer-implemented method of claim 8, wherein the portion of the data candidate includes a medical history of the medical patient, an image or video depicting the medical patient, or data produced by at least one real-time biometric sensor affixed to the medical patient.

12. The computer-implemented method of claim 8, wherein the remainder of the data candidate includes: a physician identifier associated with the medical patient; a time at which scanning of the medical patient is desired; or a hardware or software version identifier associated with the medical imaging scanner.

13. The computer-implemented method of claim 8, wherein the logical Boolean expression is user-defined.

14. The computer-implemented method of claim 8, further comprising:
generating, by the device, the logical Boolean expression based on a statistical analysis of previous manual overrides of the trained intelligent protocoling classifier.

15. A computer program product for facilitating customized exceptions for intelligent protocoling, the computer program product comprising a computer-readable memory having program instructions embodied therewith, the program instructions executable by a processor to cause the processor to:
access a data candidate associated with a medical patient;
execute a trained intelligent protocoling classifier on the data candidate, wherein the trained intelligent protocoling classifier receives as input a portion of the data candidate and does not receive as input a remainder of the data candidate, wherein the trained intelligent protocoling classifier produces as output a classification label, and wherein the classification label indicates a first medical imaging protocol to be performed by a medical imaging scanner on the medical patient;
compute a truth value of a logical Boolean expression, by applying the logical Boolean expression to the remainder of the data candidate and not to the portion of the data candidate, wherein the logical Boolean expression corresponds to a second medical imaging protocol that is different from the first medical imaging protocol; and
in response to computation of a true truth value of the logical Boolean expression, cause the medical imaging scanner to perform the second medical imaging protocol on the medical patient rather than the first medical imaging protocol.

16. The computer program product of claim 15, wherein the program instructions are further executable to cause the processor to:
in response to computation of a false truth value of the logical Boolean expression, cause the medical imaging scanner to perform the first medical imaging protocol on the medical patient rather than the second medical imaging protocol.

17. The computer program product of claim 15, wherein the program instructions are further executable to cause the processor to:
retrain the trained intelligent protocoling classifier by treating the data candidate as a training input and by treating the second medical imaging protocol as a ground-truth classification label, in response to the computation of the true truth value of the logical Boolean expression.

18. The computer program product of claim 15, wherein the portion of the data candidate includes a medical history of the medical patient, an image or video depicting the medical patient, or data produced by at least one real-time biometric sensor affixed to the medical patient.

19. The computer program product of claim 15, wherein the remainder of the data candidate includes: a physician identifier associated with the medical patient; a time at which scanning of the medical patient is desired; or a hardware or software version identifier associated with the medical imaging scanner.

20. The computer program product of claim 15, wherein the logical Boolean expression is user-defined.

* * * * *